United States Patent
Buehler

(10) Patent No.: US 7,578,912 B2
(45) Date of Patent: Aug. 25, 2009

(54) ELECTRO-ACTIVE SENSOR, METHOD FOR CONSTRUCTING THE SAME; APPARATUS AND CIRCUITRY FOR DETECTION OF ELECTRO-ACTIVE SPECIES

(75) Inventor: Martin Buehler, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 1130 days.

(21) Appl. No.: 10/750,162

(22) Filed: Dec. 30, 2003

(65) Prior Publication Data
US 2005/0016847 A1 Jan. 27, 2005

Related U.S. Application Data

(60) Provisional application No. 60/437,130, filed on Dec. 30, 2002, provisional application No. 60/513,131, filed on Oct. 21, 2003.

(51) Int. Cl.
*G01N 27/327* (2006.01)
*G01N 27/333* (2006.01)
(52) U.S. Cl. ............... 204/412; 204/403.01; 204/416
(58) Field of Classification Search ...............
204/403.01–403.15, 416–418, 412; 205/777.5, 205/778, 792
See application file for complete search history.

(56) References Cited

U.S. PATENT DOCUMENTS

| | | | | |
|---|---|---|---|---|
| 4,404,065 A | * | 9/1983 | Matson | 205/780.5 |
| 4,647,362 A | * | 3/1987 | Watanabe | 204/411 |
| 4,655,880 A | * | 4/1987 | Liu | 205/777.5 |
| 4,871,440 A | * | 10/1989 | Nagata et al. | 204/403.1 |
| 5,066,372 A | * | 11/1991 | Weetall | 506/4 |
| 5,336,388 A | * | 8/1994 | Leader et al. | 204/403.06 |
| 5,494,562 A | * | 2/1996 | Maley et al. | 257/414 |
| 5,821,399 A | * | 10/1998 | Zelin | 73/1.02 |
| 6,366,794 B1 | * | 4/2002 | Moussy et al. | 600/345 |
| 6,652,720 B1 | * | 11/2003 | Mansouri et al. | 204/403.11 |

OTHER PUBLICATIONS

Derwent abstract of Furusawa et al. JP 10-48177 A, patent published on Feb. 20, 1998.*

(Continued)

*Primary Examiner*—Alex Noguerola
(74) *Attorney, Agent, or Firm*—Tope-McKay & Associates

(57) ABSTRACT

An electro-active sensor includes a nonconductive platform with a first electrode set attached with a first side of a nonconductive platform. The first electrode set serves as an electrochemical cell that may be utilized to detect electro-active species in solution. A plurality of electrode sets and a variety of additional electrochemical cells and sensors may be attached with the nonconductive platform. The present invention also includes a method for constructing the aforementioned electro-active sensor. Additionally, an apparatus for detection and observation is disclosed, where the apparatus includes a sealable chamber for insertion of a portion of an electro-active sensor. The apparatus allows for monitoring and detection activities. Allowing for control of attached cells and sensors, a dual-mode circuitry is also disclosed. The dual-mode circuitry includes a switch, allowing the circuitry to be switched from a potentiostat to a galvanostat mode.

30 Claims, 30 Drawing Sheets

OTHER PUBLICATIONS

JPO abstract of Miyashita et al. JP 2000-19146 A, patent published on Jan. 21, 2000.*

Samuel P. Kounaves, Stefan R. Lukow, Brian P. Comeau, Michael H. Hecht, Sabrina M. Grannan-Feldman, Ken Manatt, Steven J. West, Xiaowen Wen, Martin Frant, and Tim Gillette, "The MSPO1 MECA Wet Chemistry Lab: Sensor Evaluation", Journal of Geophysical Research (Planets) Sep. 2002.

Mark Kolody, Martin G. Buehler, Gregory M. Kuhlman, Didier Keymeulen, and Nosang V. Myung, and Samuel P. Kounaves, "Planar REDOX and Conductivity Sensors for ISS Water Quality Measurements" 2003 IEEE Aerospace Conference, 2003, vol. 1, cat. No. 02TH8593C.

A. J. Bard and L. R. Faulkner, "Electrochemical Methods: Fundamentals and Applications, Second Edition", Wiley & Sons (New York, 2001).

J. Wang, Analytical Electrochemistry, Wiley-VCH, New York, 2000.

D. Diamond and V. C. A. Hanratty, Spreadsheet Applications in Chemistry using Microsoft Excel, J. Wiley & Sons (New York, 1997).

M. Pourbaix, "Atlas of Electrochemical Equilibria in Aqueous Solutions", Nation Association of Corrosion Engineers (Houston, TX 1974).

M. G. Buehler and W. R. Thurber, "A Planar Four-Probe Test Structure for Measuring Bulk Resistivity," IEEE Trans. On Electron Devices, vol. ED-23, pp. 968-974.1976.

M. G. Buehler, G. M. Kuhlman, D. Keymeulen, and S. Kounaves, "Advanced Electronic Tongue Concept", 2002 IEEE Aerospace Conference, 2002, vol. 1, cat. No. 02TH8593C.

Handbook of Chemistry and Physics, Electrochemical Series, No. 74, CRC Press (Bocaraton, 1994), No. 85.

"Microfabricated Heavy Metal Ion Sensor", G. T. A. Kovacs, C. W. Storment, and S. P. Kounaves, Sensors and Actuators B, 1995, 23, 41-47.

Y. Sakano, K. D. Pickering, P. F. Strom, and L. J. Kerkhof, "Spatial Distribution of Total, Ammonia-Oxidizing, and Denitrifying Bacteria in Biological Wastewater Treatment Reactors for Bioregenerative Life Support", Applied And Environmental Microbiology, May 2002, p. 2285-2293 vol. 68, No.

S. J. Nest, X. Wen. R. Geis, J. Herdan, T. Gillette, M. H. Hecht, W. Schubert, S. Grannan, S. P. Kounaves, "Electrochemistry on Mars," American Laboratory 31 (20), p. 48, Oct. 1999.

P. T. Kissinger and W. R. Heineman, Laboratory Techniques in Electroanalytical Chemical, Marcel Dekker (New York, 1996), Tabel of Contents only.

* cited by examiner

| Name | Compound | Molecular Weight g/mol | ppm= mg/L [5] | μM | E° V [6] |
|---|---|---|---|---|---|
| Ammonia | NH4+ | 17.03 | 0.5 | 29.360 | -0.762 |
| Arsenic | As | 75.9216 | 0.01 | 0.132 | -0.608 |
| Barium | Ba | 137.33 | 1 | 7.282 | -2.912 |
| Cadmium | Cd | 112.41 | 0.05 | 0.445 | -0.403 |
| Calcium | Ca | 40.08 | 30 | 748.503 | -3.8 |
| Chloride | Cl | 35.45 | 200 | 5641.749 | 1.358 |
| Chromium | Cr | 51.996 | 0.05 | 0.962 | -0.913 |
| Copper | Cu | 63.54 | 1 | 15.738 | 0.153 |
| Iodine | I2 | 253 | 15 | 59.289 | 0.5355 |
| Iron | Fe | 55.85 | 0.3 | 5.372 | -0.447 |
| Lead | Pb | 207.2 | 0.05 | 0.241 | -0.126 |
| Magnesium | Mg | 24.3 | 50 | 2057.613 | -2.372 |
| Manganese | Mn | 24.32 | 0.05 | 2.056 | -1.185 |
| Mercury | Hg | 200.59 | 0.002 | 0.010 | 0.851 |
| Nickel | Ni | 58.69 | 0.05 | 0.852 | -0.257 |
| Nitrate | NO3- | 62 | 10 | 161.290 | ? |
| Potassium | K | 30.1 | 340 | 11295.681 | -2.931 |
| Selenium | Se | 78.96 | 0.01 | 0.127 | -0.924 |
| Silver | Ag | 107.868 | 0.05 | 0.464 | -0.8 |
| Sulfate | SO4 | 96.07 | 250 | 2602.269 | 0.172 |
| Zinc | Zn | 65.38 | 5 | 76.476 | -0.762 |

| Sym | Reaction | E° | E°corr | Ep0 | E0 |
|---|---|---|---|---|---|
| Cu2 | Cu⁺ + e = Cu | 0.521 | 0.284 | 0.28 | .331 |
| Cu1 | Cu²⁺ + 2e = Cu | 0.342 | 0.224 | 0.133 | .141 |
| Ag | Ag₂O + H₂O + 2e = 2Ag + 2OH⁻ | 0.342 | 0.244 | 0.09 | .133 |
| Pb2 | Pb²⁺ + 2e = Pb | -0.126 | -0.244 | -0.4 | -0.349 |
| Pb1 | PbCl₂ + 2e = Pb + 2Cl⁻ | -0.2675 | -0.386 | -0.65 | -0.599 |
| Zn2 | ZnOH⁺ + H⁺ + 2e = Zn + H₂O | -0.497 | -0.615 | -0.9 | -0.849 |
| Zn1 | Zn²⁺ + 2e = Zn | -0.762 | -0.880 | -1.25 | -1.199 |

| NO. | OXIDATION REACTIONS/NERNST EQN. |
|---|---|
| A1 | $Fe = Fe^{2+} + 2e^-$ <br> $E1 = -0.440 + 0.0295 \cdot \log(Fe^{2+})$ |
| A2 | $Fe + 2H_2O = Fe(OH)_2 + 2H^+ + 2e^-$ <br> $E2 = -0.047 - 0.059 \cdot pH$ |
| A3 | $Fe(OH)_2 + H_2O = Fe(OH)_3 + H^+ + e^-$ <br> $E3 = -0.271 - 0.059 \cdot pH$ |
| A4 | $Fe = Fe^{3+} + 3e^-$ <br> $E4 = -0.037 + 0.020 \cdot \log(Fe3^+)$ |
| A5 | $Fe^{2+} + 3H_2O = Fe(OH)_3 + H^+ + e^-$ <br> $E5 = 1.057 - 0.177 \cdot pH + 0.059 \cdot \log(Fe^{2+})$ |
| A6 | $Fe^{2+} = Fe^{3+} + e^-$ <br> $E6 = 0.771$ |
| A7 | TBD |

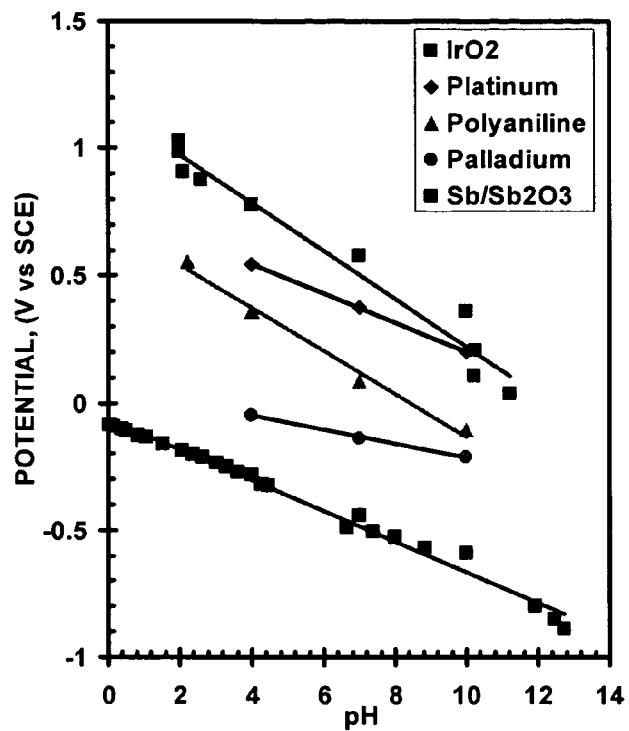

FIGURE 36

| pH Sensor | ELECTRODEPOSITION CONDITION |
|---|---|
| Polyaniline | 1 M aniline + 1 M $H_2SO_4$, pH < 1, Deposition current density = 4 mA $cm^{-2}$ |
| Platinum | 1 g/l $H_2PtCl_6$ + 176.4 g/l $H_2SO_4$, pH < 1, Deposition current density = -35 mA $cm^{-2}$ |
| Palladium | 10 g/l $Pd(NH_2)_2(NO_2)_2$ + 100 g/l ammonium sulfamate, pH = 7.5 to 8.5, Deposition current density = -1 to -20 mA $cm^{-2}$ |
| Antimony/Antimony Oxide | 20 g/l $K_2(C_4H_4O_6).3H_2O$ + 60 g/l $Na_2C_4H_4O_6.2H_2O$, pH = 7, Deposition current density = -5 to -20 mA $cm^{-2}$ |
| Iridium oxide | 1.5 g/l $H_2IrCl_6$ + 5 g/l oxalic acid [$(HCOO)_2 \cdot 2H_2O$] + 1 ml of hydrogen peroxide ($H_2O_2$), pH = 10.5, Deposition current density < 1 mA $cm^{-2}$ |

FIGURE 37

| pH Sensing Materials | Sensitivity (mV/pH) |
|---|---|
| Polyaniline | -85 |
| Platinum | -57 |
| Palladium | -32 |
| Antimony/Antimony Oxide | -55 |
| Iridium oxide | -76 |

ELECTRO-ACTIVE SENSOR, METHOD FOR CONSTRUCTING THE SAME; APPARATUS AND CIRCUITRY FOR DETECTION OF ELECTRO-ACTIVE SPECIES

PRIORITY CLAIM

This application is a non-provisional application, claiming the benefit of priority to provisional application Nos. 60/437,130 and 60/513,131, filed in the United States on Dec. 30, 2002 and Oct. 21, 2003, respectively, both titled "Electronic Tongue REDOX and Conductivity Sensors."

GOVERNMENT RIGHTS

This invention was made with Government support under Contract NAS7-1407 awarded by NASA. The Government has certain rights in the invention.

BACKGROUND OF THE INVENTION (1) Field of the Invention

The present invention relates to electro-active sensors, and more particularly, to a electro-active sensor, method for constructing the same; apparatus, and circuitry that are used to detect electro-active species in solution.

(2) Description of Related Art

Electro-active sensors have long been known in the prior art. The sensors have been used in a myriad of applications, two examples of which include detecting low-levels of electrochemically active species found in drinking water used on the International Space Station (ISS) Alpha and detecting metabolic products produced by biofilms to better understand their life-cycle activities. In pursuing these goals, a number of electrochemical cells and sensors have been developed. They include Ion Selective Electrodes (ISE's), Galvanic cells, conductivity sensors, redox cells, and pH sensors.

Redox and conductivity sensors are used to characterize ionic species in solution and are based on a traditional three-element electrochemical cell. Commercially available three-element electrochemical cells typically consist of individual pencil like metal electrodes that are placed in solution and used to detect ionic species in the solution by measuring an electrochemical cell current as voltage is scanned.

While functional, electrochemical sensors currently available suffer from several drawbacks. Traditional sensors are fabricated at an end of a pencil-like cylindrical tube. Such sensors cannot be configured easily in a multi-sensor array, nor can they be readily miniaturized.

Additionally, because of their configuration, conventional sensors generally have short useful lives, with a long life typically being one month in natural waters and up to six months in drinking waters. When used in bioreactors, the sensors typically have life expectancies of a few days. Because of their short useful lives, traditional sensors are impractical for measuring water quality in applications where testing must take place for many months or years, such as on the ISS, and during a long trip to Mars. Thus, long-life sensors that remain useful for three to five years are needed.

Therefore, it can be appreciated that there exists a need for an electrochemical cell that is planar, that is easy to clean, that lends itself to long-life usage, and that may be miniaturized. In this regard, the present invention substantially fulfills these needs.

SUMMARY OF INVENTION

The present invention relates to electro-active sensors, and more particularly, to a method and apparatus that are used to detect electro-active species in solution. The electro-active sensor is comprised of a nonconductive platform having a first side and a second side and a second side. A first electrode set is attached with the first side of a nonconductive platform. The first electrode set further comprises a first conductive via passing through the nonconductive platform from the first side to the second side; a first electrode attached with the first conductive via on the first side, where the first electrode serves as a first working electrode; a second conductive via passing through the nonconductive platform from the first side to the second side; a second electrode attached with the second conductive via on the first side, where the second electrode serves as a first reference electrode; a third conductive via passing through the nonconductive platform from the first side to the second side; and a third electrode attached with the third conductive via on the first side, where the third electrode serves as an first auxiliary electrode. The working electrode, the reference electrode, and the auxiliary electrode together serve as an electrochemical cell that may be utilized to detect the electro-active species in the solution.

In another aspect, the electro-active sensor further comprises a plurality of electrode sets. Electrical connectors may also be connected with the vias on the second side of the nonconductive platform. The electrical connectors may be connected with a monitoring apparatus, thereby allowing for monitoring of the electro-active species in the solution.

Additionally, the nonconductive platform is constructed of a material selected from a group consisting of ceramic and glass.

Furthermore, the electrodes are all formed in a substantially co-planar manner. Additionally, the electrical connectors are substantially co-planar and a plane of the electrical connectors is parallel with respect to a plane of the nonconductive platform.

At least a portion of each electrode in the electrode set is formed in a shape selected from a group consisting of a ring and a disk. Additionally, each electrode set may be formed such that the electrodes in the electrode set are concentric. When concentric, the reference electrode surrounds the working electrode, and the auxiliary electrode surrounds the reference electrode.

The first auxiliary electrode from the first electrode set may be connected with a second auxiliary electrode from a second electrode set. When connected, the first and the second auxiliary electrodes may be connected with a common ground.

The electro-active sensor further comprises a biofilm attached with the first side of the nonconductive platform. Additionally, the electro-active sensor further comprises an Ion Selective Sensor attached with the first side of the nonconductive platform, where the Ion Selective Sensor may be a pH sensor.

Additionally, the electro-active sensor further comprises a four-terminal conductivity sensor attached with the first side of the nonconductive platform, thereby allowing for a measurement of a conductivity of the solution.

Furthermore, electro-active sensor further comprises a two-terminal heater attached with the nonconductive platform, thereby allowing the electro-active sensor to be heated to varying temperatures. In order to monitor a temperature of the platform, a two-terminal temperature sensor may be attached with the nonconductive platform.

In another aspect, the electro-active sensor further comprises circuitry attached with the electrical connectors. The circuitry further comprises a potentiostat circuit portion attached with an electrochemical cell, the electrochemical cell comprising a grounded auxiliary electrode, a reference electrode, and a working electrode, whereby when activated, the potentiostat circuit portion forces a voltage between the working electrode and the reference electrode; a feedback circuit connected with the potentiostat circuit portion, whereby when the potentiostat circuit portion is activated, the feedback circuit adjusts a current though the electrochemical cell accordingly; a galvanostat circuit portion attached with the electrochemical cell, whereby the galvanostat circuit portion forces a current through the electrochemical cell and when the galvanostat circuit portion is activated the feedback circuit adjusts a voltage between the working electrode and the reference electrode; and a switch circuit connected with the potentiostat circuit portion and galvanostat circuit portion, allowing for the activation of the potentiostat or galvanostat circuit portion.

The present invention also comprises a method for constructing an electro-active sensor for detecting electro-active species in solution. The method comprises an act of forming a first electrode set on a first side of a nonconductive platform. The of forming the first electrode set further comprises acts of forming a first electrode on a first side of a nonconductive platform, the first electrode serving as a working electrode; forming a first via from the first side to a second side of the nonconductive platform, wherein the first via is attached with the first electrode; forming a second electrode on the first side of the nonconductive platform, the second electrode serving as a reference electrode; forming a second via from the first side to the second side of the nonconductive platform, wherein the second via is attached with the second electrode; forming a third electrode on the first side of the nonconductive platform, the third electrode serving as an auxiliary electrode; and forming a third via from the first side to the second side of the nonconductive platform, wherein the third via is attached with the third electrode, whereby if a solution is placed on the first side of the nonconductive platform, the working electrode, the reference electrode and the auxiliary electrode may be utilized to detect an electro-active species in the solution.

The method further comprises an act of forming a second electrode set on the first side of the nonconductive platform.

In another aspect, the method further comprises an act of forming electrical connectors attached with the vias on the second side of the nonconductive platform, whereby the electrical connectors may be connected with a monitoring apparatus, allowing for detection of the electro-active species in the solution.

In the act of forming an electrode on the first side of the nonconductive platform, the act further comprises acts of depositing a conductive material on the first side of the nonconductive platform; and curing the electrically conductive material to affix the conductive material to the nonconductive platform.

In the act of forming a via from the first side to the second side of the nonconductive platform, the act further comprises acts of forming a via through the nonconductive platform from the first side to the second side of the nonconductive platform; depositing a conductive material over the via; creating an electrically conductive via by drawing the conductive material through the via; and curing the electrically conductive material to affix the conductive material with the first side of the nonconductive platform, with the second side of the nonconductive platform, and with the walls of the via, thereby creating the via.

In the act of forming electrical connectors attached with the vias, the act further comprises acts of depositing a conductive material on the second side of the nonconductive platform, such that the material is in contact with the vias; curing the conductive material to affix the conductive material with both the second side of the nonconductive platform and with the vias.

In the act of forming an electrode on the first side of the nonconductive platform, the act further comprises an act of selecting a non-conductive platform constructed of a material selected from a group consisting of ceramic and glass.

In the act of forming the first electrode set on the first side of the nonconductive platform, the electrodes are formed such that they are substantially planar.

In the act of forming electrical connectors attached with the vias on the second side of the nonconductive platform, the electrical connectors are formed such that they are substantially planar, with a plane of the electrical connectors being parallel with a plane of the nonconductive platform.

In the act of forming the electrode sets, at least a portion of each electrode in the electrode set is formed in a shape selected from a group consisting of a ring and a disk. Additionally, each electrode in the electrode sets are formed such that the electrodes are concentric.

In the acts of forming the electrode sets, the reference electrode is formed such that it surrounds the working electrode, and the auxiliary electrode is formed such that it surrounds the reference electrode.

Furthermore, in the act of forming the second electrode set on the first side of the nonconductive platform, a second auxiliary electrode from the second electrode set is formed such that it is connected with the first auxiliary electrode from the first electrode set.

In the act of forming the first and second auxiliary electrodes, they are formed such that they are connected with a common ground.

The method further comprises an act of forming a biofilm on the first side of the nonconductive platform.

Additionally, the method further comprises an act of forming an Ion Selective Sensor on the first side of the nonconductive platform, where the Ion Selective Sensor is a pH sensor.

In another aspect, the method further comprises an act of forming a four-terminal conductivity sensor on the first side of the nonconductive platform, thereby allowing for measurement of conductivity of the solution.

The method further comprises an act of forming two-terminal heater on the second side of the nonconductive platform, thereby allowing the electro-active sensor to be heated to varying temperatures.

Additionally, the method comprises an act of forming a two-terminal temperature sensor on the second side of the nonconductive platform, thereby allowing for monitoring of a temperature of the electro-active sensor.

The present invention also includes an electro-active species detection and observation apparatus. The apparatus comprises a fluid-tight first sealable chamber for sealing at least a portion of an electro-active sensor within an interior of the sealable chamber, the electro-active sensor having electrodes on the portion of the electro-active sensor sealed within the first sealable chamber; a first inlet port connected with the first sealable chamber; and a first outlet port connected with the first sealable chamber, whereby a solution may be introduced into the first sealable chamber through the inlet port and exit through the outlet port, thereby allowing for detection and measurement of an electro-active species within the solution as it flows through the first sealable chamber.

The apparatus further comprises a first window attached with the first sealable chamber, thereby allowing for observation of the interior of the sealable chamber. The window is constructed such that it is capable of receiving an objective of a microscope.

In another aspect, the apparatus further comprises a fluid spreader connected with the inlet port, where the solution is introduced to the fluid spreader before being introduced to a remainder of the sealable chamber, thereby eliminating bubbles and allowing the solution to be uniformly spread.

Additionally, the apparatus further comprises a first O-ring and a second O-ring, the first O-ring and the second O-ring being attached with the sealable chamber, whereby the portion of the electro-active sensor having electrodes may be placed between the first O-ring and the second O-ring, thereby sealing a chamber with the top side of the electro-active sensor.

In another aspect, the apparatus further comprises a monitoring apparatus with circuitry for attaching with the electro-active sensor. The circuitry comprises a potentiostat circuit portion capable of being attached with an electrochemical cell, the electrochemical cell comprising a grounded auxiliary electrode, a reference electrode, and working electrode, whereby the potentiostat circuit portion forces a voltage between the working electrode and the reference electrode; a feedback circuit operable with the potentiostat circuit portion, whereby when the potentiostat circuit portion is activated, the feedback circuit adjusts a current though the electrochemical cell accordingly; a galvanostat circuit portion capable of being attached with the electrochemical cell, whereby the galvanostat circuit portion forces a current through the electrochemical cell and when the galvanostat circuit portion is activated the feedback circuit adjusts a voltage between the working electrode and the reference electrode; and a switch circuit connected with the potentiostat and galvanostat portion, allowing for the activation of the potentiostat or galvanostat circuit portion.

In yet another aspect, the apparatus further comprises a fluid-tight second sealable chamber for sealing at least a portion of an electro-active sensor within an interior of the second sealable chamber, the electro-active sensor having electrodes; a second inlet port connected with the second sealable chamber; and a second outlet port connected with the second sealable chamber, whereby a solution may be introduced into the second sealable chamber through the second inlet port and exit through the second outlet port, thereby allowing utilization of both the first sealable chamber and the second sealable chamber to conduct multiple tests.

The apparatus further comprises a second window attached with the second sealable chamber, thereby allowing for observation of an interior of the second sealable chamber.

Additionally, a micro-fluidics system is attached with both the first sealable chamber and the second sealable chamber, allowing for control of the solution applied to each chamber.

The present invention also includes a dual mode circuitry for attaching with an electrochemical cell. The circuitry comprises a potentiostat circuit portion capable of being attached with an electrochemical cell, the electrochemical cell comprising a grounded auxiliary electrode, a reference electrode, and a working electrode, whereby the potentiostat circuit portion forces a voltage between the working electrode and the reference electrode; a feedback circuit operable with the potentiostat circuit portion, whereby when the potentiostat circuit portion is activated, the feedback circuit adjusts a current though the electrochemical cell accordingly; a galvanostat circuit portion capable of being attached with the electrochemical cell, whereby the galvanostat circuit portion forces a current through the electrochemical cell and when the galvanostat circuit portion is activated, the feedback circuit adjusts a voltage between the working electrode and the reference electrode; and a switch circuit connected with the potentiostat and galvanostat portion, allowing for the activation of the potentiostat or galvanostat circuit portion.

The potentiostat circuit portion comprises a first instrumentation amplifier having a first input, a second input and an output, with the first input connected with the reference electrode, the second input connected with the working electrode, and the output connected with the switch circuit.

The galvanostat circuit portion comprises a second instrumentation amplifier having a first input, a second input and an output, with the first input connected to the working electrode, at least one resistor, the second input connected with the working electrode through the at least one resistor, and the output connected with the switch circuit.

The feedback circuit comprises an operational amplifier having a first input, a second input and an output, with the first input connected with an output of the switch circuit, the second input connected with a digital to analog converter, and the output connected with the working electrode.

BRIEF DESCRIPTION OF THE DRAWINGS

The nature of the electro-active sensor, the method for constructing the electro-active sensor, the electro-active species detection and observation apparatus, and the dual mode circuitry for detection of electro-active species described herein will be readily apparent with reference to the description below taken in conjunction with the following drawings, in which:

FIG. 36 is a graph illustrating pH responses of various sensing materials where a saturated calomel electrode was used as a reference electrode;

FIG. 37 is a table illustrating electro-deposition conditions for various pH sensing materials;

DETAILED DESCRIPTION

Figure 1A:
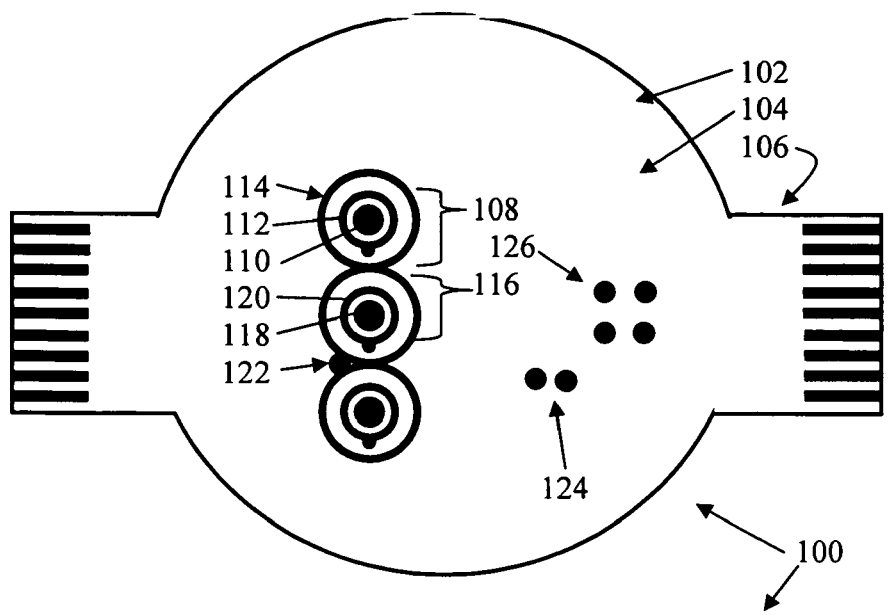
FIG. 1A is an illustration of a top view of an electro-active sensor according to the present invention.

The present invention relates to electrochemical sensors, and more particularly, to a method and apparatus that are used to detect electro-active species in solution by measuring an electrochemical cell current as a voltage is scanned.

The following description, taken in conjunction with the referenced drawings, is presented to enable one of ordinary skill in the art to make and use the invention. Various modifications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein. Furthermore, it should be noted that unless explicitly stated otherwise, the figures included herein are illustrated qualitatively and without any specific scale, and are intended to generally present the concept of the present invention.

In order to provide a working frame of reference, first a glossary of terms used in the description and claims is given as a central resource for the reader. Next, a discussion of various aspects of the present invention is provided to give an understanding of the specific details.

(1) Glossary

Before describing the specific details of the present invention, a centralized location is provided in which various terms used herein and in the claims are defined. The glossary provided is intended to provide the reader with a general understanding for the intended meaning of the terms, but is not intended to convey the entire scope of each term. Rather, the glossary is intended to supplement the rest of the specification in more clearly explaining the terms used.

Electrochemical Cell—The term "Electrochemical Cell" refers to an electrode sensor that may be used to detect ionic species in a solution. The term "Electrochemical Cell" may be used interchangeably with the term "redox sensor."

Redox sensor—The term "redox sensor" refers to one type of electrochemical cell of the present invention and may be used interchangeably with the term "Electrochemical Cell."

WE—The term "WE" refers to a working electrode. In many electrochemical experiments, the working electrode may be an inert material such as gold, platinum or glassy carbon. In some circumstances, the working electrode may serve as a surface on which the electrochemical reaction takes place. In corrosion testing, the working electrode may generally be a sample of the corroding material.

RE—The term "RE" refers to a reference electrode. The reference electrode may be used in measuring the working electrode potential.

AE—The term "AE" refers to an auxiliary electrode. An auxiliary electrode may be a conductor that completes a three electrode (i.e. WE, RE, and AE) electrochemical cell circuit. Current that flows into the solution via the working electrode leaves the solution via the auxiliary electrode.

(2) Introduction

Electrochemical cells utilize metal electrodes as sensors to detect electro-active species in solution by measuring an electrochemical cell current as a voltage is scanned. For example, redox, pH, and conductivity sensors may be used in analysis of ionic species found in natural and drinking water. The cells may be used for several measurements, non-limiting examples of which include conductivity measurements that provide a gross indication of ions present in a solution, Cyclic Voltammetry that provides a survey of electro-active species, and Anodic Stripping Voltammetry (ASV) that allows ion identification and quantification. Such techniques allow for the detection of a variety of ions, non-limiting examples of which include Zn, Fe, Pb, Cu, and Ag. The invention disclosed herein describes an electro-active sensor, a method for forming the electro-active sensor, an electro-active species detection and observation apparatus, potentiostat and galvanostat circuitry, a measurement methodology, and various applications to water quality measurements.

(3) Electro-Active Sensor

Electro-active sensors utilize electrochemical cells and other sensors to detect electro-active species in solution. In previous electro-active sensor designs, access to the sensor electrodes was achieved by a series of pins attached with an underside of a ceramic substrate or platform. Such an approach was unacceptable given microscope height restrictions. The sensor presented herein was designed to be planar utilizing edge connectors that are attached with flex cables to associated electronics, thus it can accommodate the height restrictions imposed by a microscope. This design approach has an additional benefit of allowing the substrate to be heat sterilizable since all materials used in its fabrication are fired at a high temperature, usually at least 850° C. This is important in microbial studies where sterility can be a critical issue. A detailed description of the sensor of the present invention is presented next.

A top view of the electro-active sensor 100 disclosed herein is illustrated in FIG. 1A. The electro-active sensor 100 comprises a nonconductive platform 102 having a first side 104 and a second side 106. The nonconductive platform 102 may be any suitably nonconductive substrate, non-limiting examples of which include ceramic and glass.

The electro-active sensor 100 may contain a variety of sensors and cells. For example, a first set of electrodes 108, e.g. a redox sensor, is formed on the first side 104 of the nonconductive platform 102. The set of electrodes 108 is comprised of a first electrode 110 (first Working Electrode (first WE)), a second electrode 112 (first Reference Electrode (first RE)), and a third electrode 114 (first Auxiliary Electrode (first AE)).

The first WE 110, RE 112 and AE 114 serve as an electrochemical cell (redox sensor) that may be utilized to detect an electro-active species in a solution. In a non-limiting example of an operational use, the redox sensor may be biased so that ions flow between the WE 110 and the AE 114. The RE 112 senses the potential between the WE 110 and AE 114. Thus, the measured voltage is the potential drop across a double layer (i.e. transition zone between an electrode and a solution) at the WE 110 and the series resistance of the electrolyte between the WE 110 and the RE 112.

The electro-active sensor 100 may include a plurality of electrode sets. For example, a second electrode set 116, e.g., redox sensor, may be formed on the first side 104 of the nonconductive platform 102. The second electrode set 116 comprises a fourth electrode 118 (second Working Electrode (second WE)), a fifth electrode 120 (second Reference Electrode (second RE)), and a sixth electrode 122 (second Auxiliary Electrode (second AE)). When the second electrode set 116 is formed, the first AE 114 may be electrically connected with the second AE 122. As a non-limiting example, the first AE 114 and the second AE 122 may be connected to a common ground.

The electrodes may be formed in any suitable shape or form, non-limiting examples of which include rings, disks and bars. For example, and as illustrated in FIG. 1A, each electrode 110, 112, 114, 118, 120, and 122 in the electrode sets may be fabricated on the nonconductive platform 102 such that they are substantially planar. Further, the electrodes may be fabricated as concentric circles, with the first WE 110 being formed as a disk, and the first RE 112 and the first AE 114 electrodes being rings about the disk.

Additionally, the second electrode set 116 may take substantially the same form as the first electrode set 108, where the electrodes are shaped as concentric rings and a disk.

In another example, the electrodes can be bars, where any reference electrode 112, and 120 must be placed between a respective working electrode 110, and 118 and a respective auxiliary electrode 114, and 122.

The electrodes and sensors may be constructed of any suitably conductive material, non-limiting examples of which include the first and second WE's 110, and 118 being Au(12) Pt(88), the first and second RE's 112, and 120 being Pd(12) Ag(88), and the first and second AE's 114, and 122 being Au(12)Pt(88). Further, the electrodes and sensors may be constructed in any suitable dimension, non-limiting examples of which include the first and second WE's 110, and 118 having a diameter of 0.75 mm, the first and second RE's 112, and 120 being 0.25 mm wide and separated from the other electrodes by 0.25 mm, and the first and second AE's 114, and 122 having an inner diameter of 2.75 mm.

An aspect of the present invention is when the first AE 114 is electrically connected with the second AE 122, and is common with both the first 108 and second 116 electrode sets. This feature reduces the number of pins or wires from the cell pair and reduces the wire count when the cells are connected in large arrays. The shared AE 114, and 122 may serve as any suitable form of an electrical connection, a non-limiting example of which includes being a ground. When the shared AE 114, and 122 is grounded, each sensor is intrinsically isolated, so that their electric fields do not interfere. Another advantage of a grounded AE 114, and 122 pair is a ground plane for the entire cell is provided that acts as an electrical shield to reduce noise. The common, grounded AE 114, and 122 feature of this electrochemical cell design may be extended to arrays with many electrochemical cells.

The electro-active sensor 100 may also include a variety of additional sensors attached with the nonconductive platform 102, non-limiting examples of which include a two-terminal (two-electrode) Ion Selective Sensor 124 such as a pH sensor, and a four-terminal (four-electrode) conductivity sensor 126. The Ion Selective Sensor 124 may use its two-terminals to measure an amount of ions present in a solution by providing a path between one terminal and the other terminal.

Figure 1B:
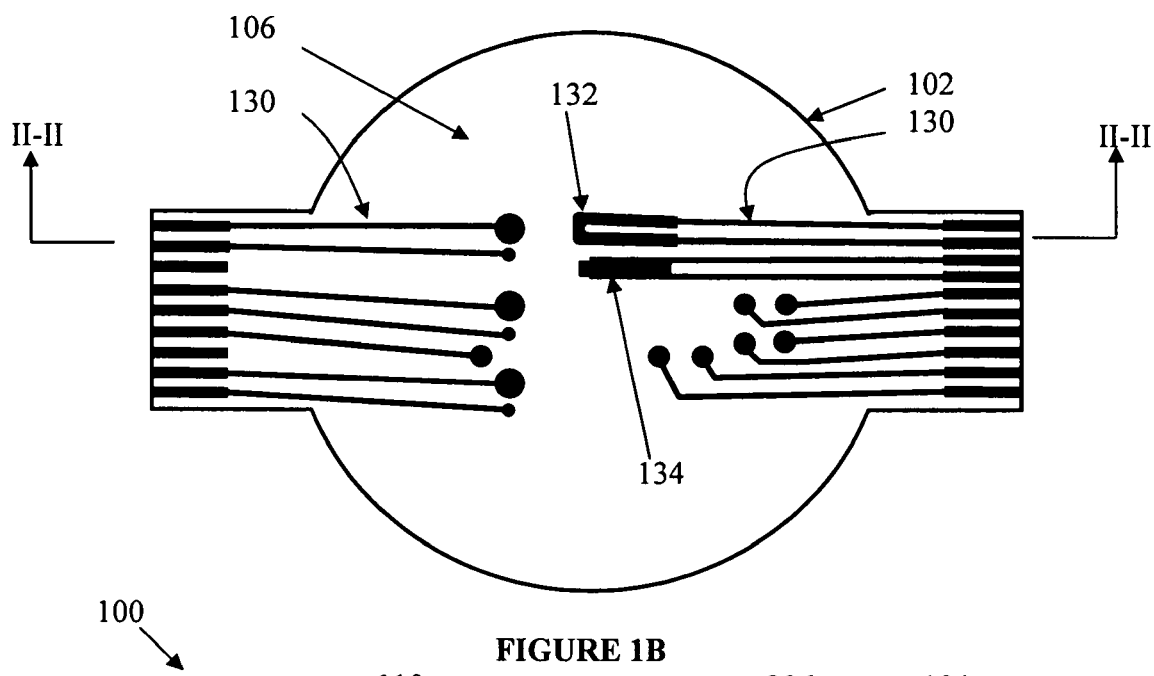
FIG. 1B is an illustration of a bottom view of an electro-active sensor according to the present invention.

FIG. 1B illustrates a bottom side 106 of the electro-active sensor 100. As illustrated in FIG. 1B, at least one second side electrical connector 130 is formed on the bottom side 106 of the electro-active sensor 100. The second side electrical connector 130 may be constructed of any suitable conductive material, non-limiting examples of which include gold, platinum, and silver. The second side electrical connector 130 can be connected with a monitoring/analysis apparatus, allowing for monitoring or analysis of electro-active species in a solution. The nonconductive platform 102 may contain any suitable number of second side electrical connectors 130, where each second side electrical connector 130 is connected with a via 200.

Furthermore, a heater 132 and temperature sensor 134 may be attached with the electro-active sensor 100, thereby allowing the electro-active sensor 100 to be heated to varying temperatures. The heater 132 may be any suitable heating mechanism or device, a non-limiting example of which includes a two-terminal heater attached with the nonconductive platform 102. The two-terminal heater 132 may be a conductive material affixed to the nonconductive platform 102, such that electricity passes through the conductive material in order to heat the platform 102. The temperature sensor 134 may be any suitable mechanism or device for measuring temperature, a non-limiting example of which includes a two-terminal thermometer comprised of a conductive material affixed to the platform 102, where the conductive material transfers a temperature of the platform 102 to monitoring/analyzing apparatus. The heater 132 may be used to heat the nonconductive platform 102, while the temperature sensor 134 is used to monitor its temperature.

Figure 2:
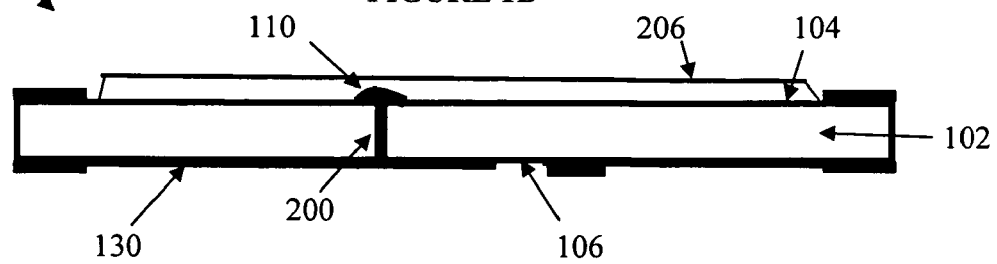
FIG. 2 is an illustration of a cut-away, cross-sectional view taken from line II-II of FIG. 1B, of an electro-active sensor according to the present invention.

FIG. 2 illustrates a cut-away cross-sectional view, taken from line II-II of FIG. 1B, of an electro-active sensor 100. As shown in FIG. 2, a via 200 electrically connects the electrodes, such as the first electrode 110, from the first side 104 of the nonconductive platform 102 with a second side electrical connector 130 on the second side 106 of the nonconductive platform 102.

In another aspect, a biofilm 206 may be attached with the first side 104 of the nonconductive platform 102. The biofilm 206 may be deposited on the nonconductive platform 102 to monitor/analyze numerous properties and characteristics, non-limiting examples of which include monitoring/analyzing growth and corrosive properties of any biological substrate included in the biofilm 206.

The biofilm 206 may be depositing through any suitable technique for microbial deposition, a non-limiting example of which includes (1) introducing the biofilm 206 medium to the electro-active sensor 100 in a planktonic state, (2) stopping the flow of the biofilm 206 medium to allow the biofilm 206 attach to a surface of the electro-active sensor 100, and (3) resuming the flow of the medium to leave the biofilm 206 behind. Additionally, the biofilm 206 may contain any suitably sized microorganisms, a non-limiting example of which includes S.mutans.

FIG. 2 illustrates a non-limiting example of an electrode shape, where each electrode, such as the first electrode 110, can be substantially planar. Additionally, as a non-limiting example, each second side electrical connector 130 can be substantially planar. Furthermore, as a non-limiting example, the planes of the second side electrical connector 130, an electrode such as the first electrode 110, and the nonconductive platform 102 can be substantially parallel.

An advantage of the planar properties of the electro-active sensor 100 shown is that it allows the sensor 100 to be fabricated with a vertical dimension that enables it to be fitted to a stage of a microscope. Through being viewable under a microscope, the sensor 100 may be easily checked for corrosion and other visual properties of the sensors and biofilm.

(4) Forming the Electro-Active Sensor

FIGS. 3A-3F illustrate formation of an electro-active sensor 100 for detecting electro-active species in a solution. The electro-active sensor 100 may be formed through any suitable method for forming an electro-active sensor 100, a non-limiting example of which includes using hybrid microelectronic fabrication methods.

Figure 3A:
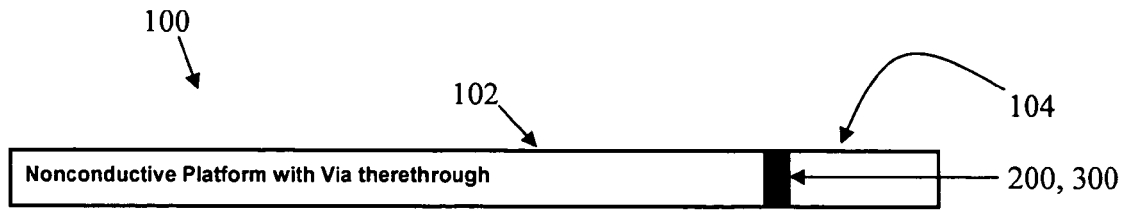
FIG. 3A is an illustration of a cross-sectional side-view of electro-active sensors, showing formation of a via therethrough.

As shown in FIG. 3A, a via 200 is formed from the first side 104 of the nonconductive platform 102, to the second side 106 of the nonconductive platform 102. The via 200 may be formed through any suitable technique for creating a via through a substrate, a non-limiting example of which includes laser drilling.

Once the via 200 is formed, a conductive material 300 is deposited over the via. The conductive material 300 is deposited over the via 200 by any suitable technique for depositing a material, a non-limiting example of which includes screen-printing. The conductive material 300 may be any suitably conductive material, non-limiting examples of which include platinum, silver, and gold.

The via 200 is made into a conductive via 200 by drawing the conductive material 300 through the via 200. The conductive material 300 is drawn through the via 200 by any suitable technique for drawing a material through a via 200, a non-limiting example of which includes using a vacuum.

Once the conductive material 300 is drawn through the via 200, the conductive material is cured to affix it with the walls of the via 200. The conductive material 300 affixed through any technique for curing one material with another, a non-limiting example of which includes firing the platform 102 with the layer of conductive material 300 in an air atmosphere at least 850° C.

Figure 3B:
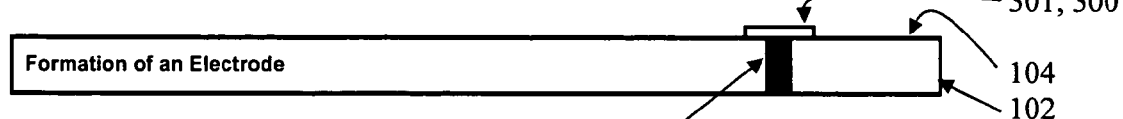
FIG. 3B is an illustration of a cross-sectional side-view of electro-active sensors, showing formation of an electrode.

As shown in FIG. 3B, an electrode 301 (such as any of the previously mentioned electrodes, i.e. first WE, first RE, first AE, and terminal points, etc.) is formed on the first side 104 of the nonconductive platform 102. Each electrode 301 is positioned such that it may be connected with a via 200, or alternatively, a via 200 is positioned such that it may be connected with an electrode 301. The electrode 301 is formed by depositing a conductive material 300 on the platform 102, where it is thereafter cured to be affixed with the platform 102.

Figure 3C:
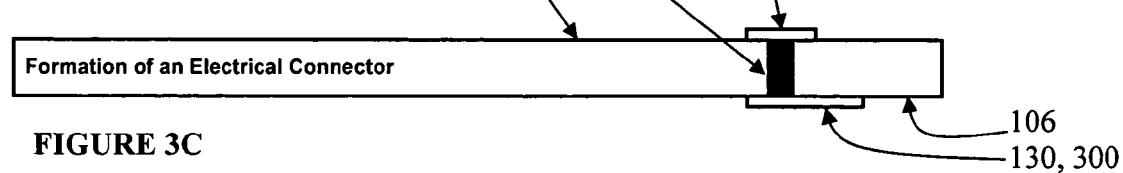
FIG. 3C is an illustration of a cross-sectional side-view of electro-active sensors, showing formation of an electrical connector on a second side of a nonconductive platform.

As shown in FIG. 3C, a second side electrical connector 130 is attached with the via 200 on the second side 106 of the nonconductive platform 102 through deposition of a conductive material 300. The material is deposited such that the conductive material 300 is in contact with the via 200, thereby electrically connecting the electrode 301 with the electrical connector 130. After deposition, the conductive material 300 is therafter cured to be affixed with the platform 102.

Figure 3D:
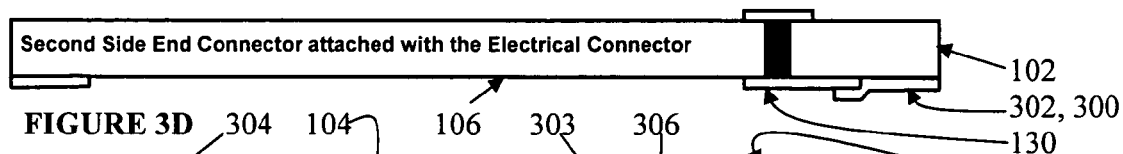
FIG. 3D is an illustration of a cross-sectional side-view of electro-active sensors, showing formation of a second side end connector.

As shown in FIG. 3D, a second side end connector 302 may be attached with the second side electrical connector 130 through deposition of a conductive material 300. The second side end connector 302 is deposited such that the conductive material 300 is in contact with the second side electrical connector 130, thereby electrically connecting the electrode 301 with the second side end connector 302. Once deposited, the conductive material 300 is thereafter cured to affix it with the second side 106 of the nonconductive platform 102.

Figure 3E:
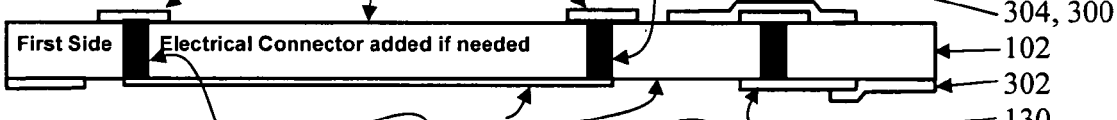
FIG. 3E is an illustration of a cross-sectional side-view of electro-active sensors, showing formation first side electrical connector.

In some aspects and as shown in FIG. 3E, the electro-active sensor 100 may include an additional electrode 303. When the number of additional electrodes 303 is numerous, space on the second side 106 of the nonconductive platform 102 for second side end connectors 302 may be limited. As shown in FIG. 3E, in order to allow for additional electrodes 303, a first side electrical connector 304 may be added to the first side 104 of the nonconductive platform 102 through deposition of a conductive material 300, which is thereafter cured to be affixed with the nonconductive platform 102.

The first side electrical connector 304 may be attached with the nonconductive platform 102 and an additional electrode 303 in any suitable manner to allow for more space, non-limiting examples of which include being attached with the additional electrode 303 on the first side 104 of the nonconductive platform 102, or being attached with a second via 305 that passes from the second side 106 to the first side 104 of the nonconductive platform 102.

When attached with a second via 305 that passes from the second side 106 to the first side 104 of the nonconductive platform 102, the second via 305 is electrically connected with the additional electrode 303 by a second side electrical connector 130 and third via 306.

Figure 3F:
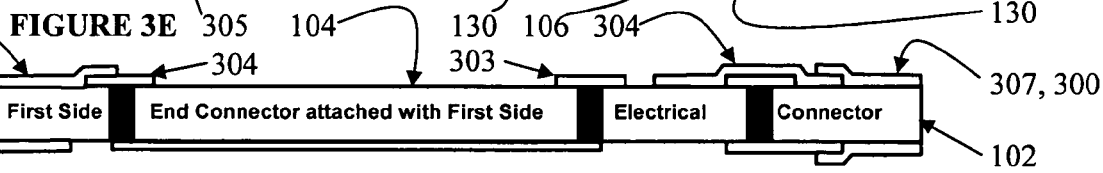
FIG. 3F is an illustration of a cross-sectional side-view of electro-active sensors, showing formation of a first side end connector.

As shown in FIG. 3F, a first side end connector 307 may be added to the electro-active sensor 100 through deposition of a conductive material 300 that is electrically connected with the first side electrical connector 304. The conductive material 300 is therafter cured to be affixed with the nonconductive platform 102.

(5) Electro-Active Species Detection and Visualization Apparatus

Figure 4A:
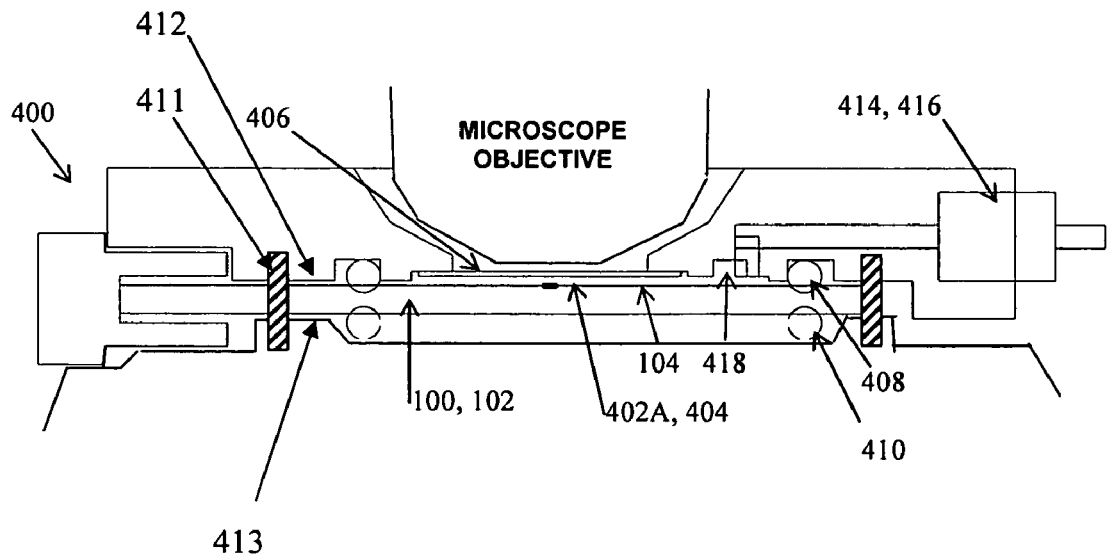
FIG. 4A is an illustration of a cut-away, cross-sectional side view of an electro-active species detection and observation apparatus according to the present invention.

An electro-active species detection and observation apparatus 400 is shown in FIG. 4A. The apparatus 400 is used to seal electrochemical cells and sensors within a chamber. A solution may be introduced into the chamber and thereafter to the electrochemical cells and sensors, thereby allowing for detection and measurement of an electro-active species within the solution as it flows through the chamber.

The apparatus 400 includes a fluid-tight first sealable chamber 402A for sealing at least a portion of an electro-active sensor 100 within an interior 404 of the first sealable chamber 402A. In order to view the interior 404 of the chamber 402A, the apparatus 400 also includes a first window 406 attached with the first sealable chamber 402A. The first window 406 is constructed such that it is capable of receiving an objective of a microscope, thereby allowing for detailed observation of the portion of the electro-active sensor 100 placed within the interior 404.

The first sealable chamber 402A is sealed through use of any suitable mechanism or device for sealing a chamber. For example, the apparatus 400 may include a first O-ring 408 and a second O-ring 410. When utilizing O-rings, a portion of the electro-active sensor 100 having electrodes 301 may be placed between the first O-ring 408 and the second O-ring 410. The O-rings 408, 410 are detachably attachable, allowing the first sealable chamber 402A to be opened and closed so that the electro-active sensor 100 may be inserted or replaced. The O-rings are thereafter clamped into place by any suitable technique, e.g., screws 411 connecting a first portion 412 with a second portion 413, thereby sealing a chamber between the first side 104 of the electro-active sensor 100 and the first window 406.

Not only do the O-rings provide for a water-tight seal, but because of a delicate nature of the electro-active sensor 100, the use of two O-rings does not place a bending stress on the nonconductive platform 102, as the nonconductive platform 102 can potentially crack if subjected to a bending moment.

The first sealable chamber 402A also includes a first inlet port 414 and a first outlet port 416. Once sealed, a solution may be introduced into the first sealable chamber 402A through the first inlet port 414. The solution is thereafter introduced to an optional fluid spreader 418, where the solution is spread before it is passed on to the remainder of the first sealable chamber 402A, thereby eliminating bubbles and allowing the solution to be uniformly spread across the electro-active sensor 100. The fluid spreader 418 may be any suitable mechanism or device for spreading a solution, a non-limiting example of which includes an arched groove that must be filled before allowing a solution to uniformly leave the groove.

After having passed through the first sealable chamber 402A, the solution may exit the chamber through the first outlet port 416. Through use of the first inlet port 414 and the first outlet port 416, the chamber may be configured as a flow through chamber, where a solution may be introduced, examined, and then removed to allow for examination of another solution.

Figure 4B:
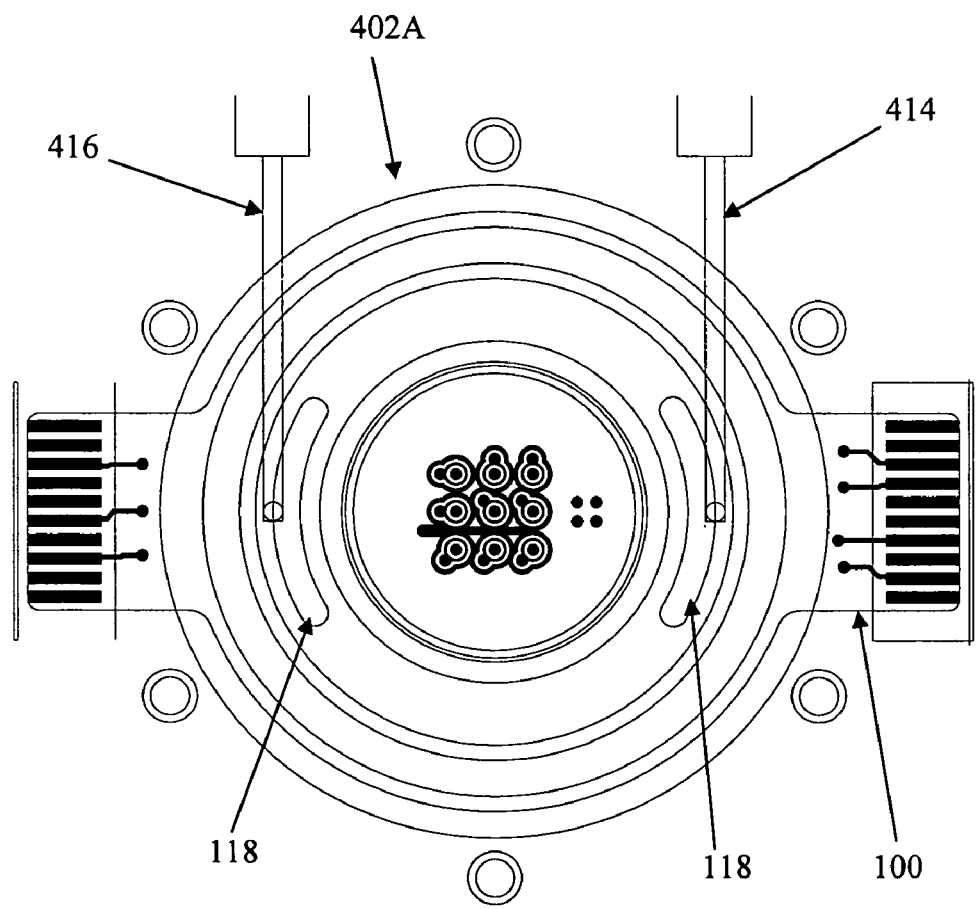
FIG. 4B is an illustration of a cut-away, top view of an electro-active species detection and observation apparatus according to the present invention.

FIG. 4B illustrates a cut-away top view of the first sealable chamber 402A, with an electro-active sensor 100 inserted therein. As shown in FIG. 4B, a solution can be introduced to the fluid spreader 418 from the first inlet port 414. The solution thereafter passes through the first sealable 402A and exits through the first outlet port 416.

Figure 5:
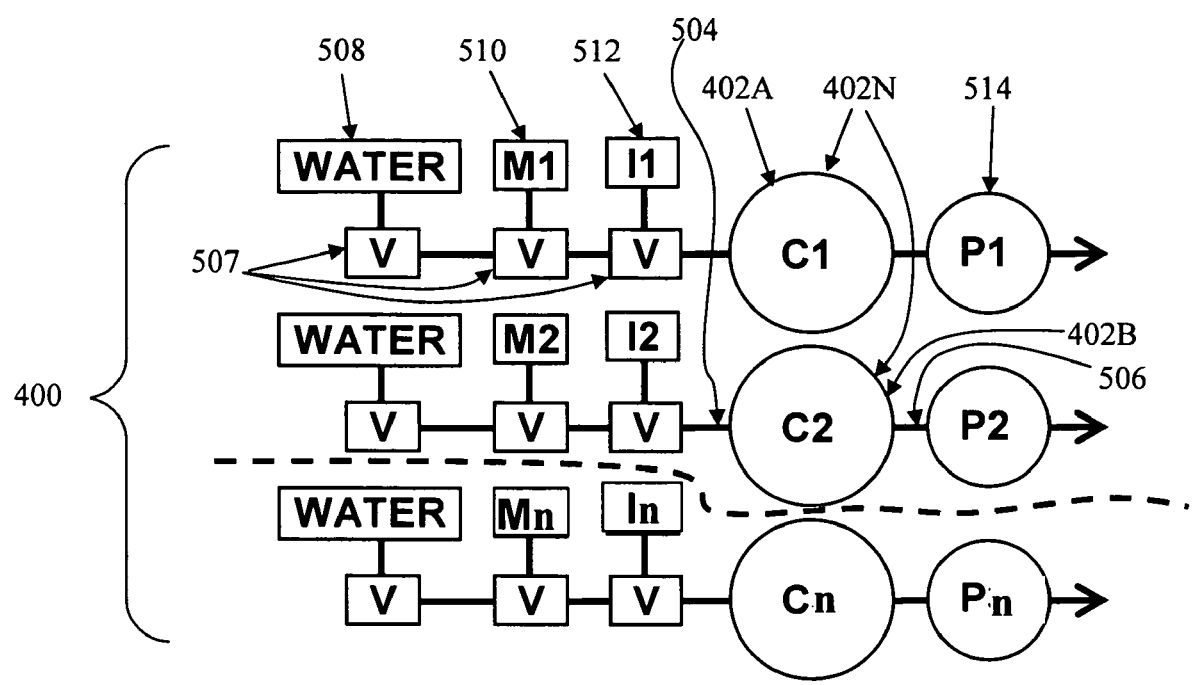
FIG. 5 is a block diagram of combinatrics and a micro-fluidics system according to the present invention.

Another advantage of utilizing a sealable chamber is that it allows for combinatrics, where a plurality of sealable chambers may be utilized to conduct multiple tests. For example, and as shown in FIG. 5, the apparatus 400 may include multiple sealable chambers 402N (where "N" in an alphabetical index for the system to which the sealable chamber corresponds). In this application, the apparatus 400 may further comprise a fluid-tight second sealable chamber 402B for sealing at least a portion of an electro-active sensor within an interior of the second sealable chamber 402B. The second sealable chamber 402B may include all of the same components as the first sealable chamber 402A, non-limiting examples of which include a second inlet port 504 and a second outlet port 506.

A solution may be introduced into the second sealable chamber 402B through the second inlet port 504 and exit through the second outlet port 506, thereby allowing for utilization of both the first sealable chamber 402 and the second sealable chamber 402B to conduct multiple tests. The combinatric technique described herein may be multiplied ad infinitum, and is not limited to a first 402A and second 402B sealable chambers, nor is it limited to three sets of components as shown in FIG. 5.

A micro-fluidic system may be attached with the sealable chambers 402N, thereby allowing for control of the solution applied to each chamber. As illustrated in FIG. 5, valves 507 (labeled as "V" in FIG. 5) are used to control contents of the solution. After controllably passing through a valve 507, water 508 (labeled as "Water" in FIG. 5), a medium 510 (labeled as "Mn" in FIG. 5, where n is a number of the system to which M corresponds), and an innoculant 512 (labeled as "In" in FIG. 5, where n is a number of the system to which I corresponds) may be pulled through a sealable chamber 402N (labeled as "Cn" in FIG. 5, where n is a number of a system to which C corresponds) through use of a pump 514 (labeled as "Pn" in FIG. 5, where n is a number of the system to which P corresponds).

The pump 514 pulls the solution through an inlet port such as the second inlet port 504 and into a chamber, such as the second sealable chamber 402B. The solution thereafter flows through the sealable chamber 402B, where it exits through an outlet port, such as the second outlet port 506. Upon exiting the sealable chamber 402B, the solution may by disposed of or collected for further analysis and experimentation.

Figure 6:
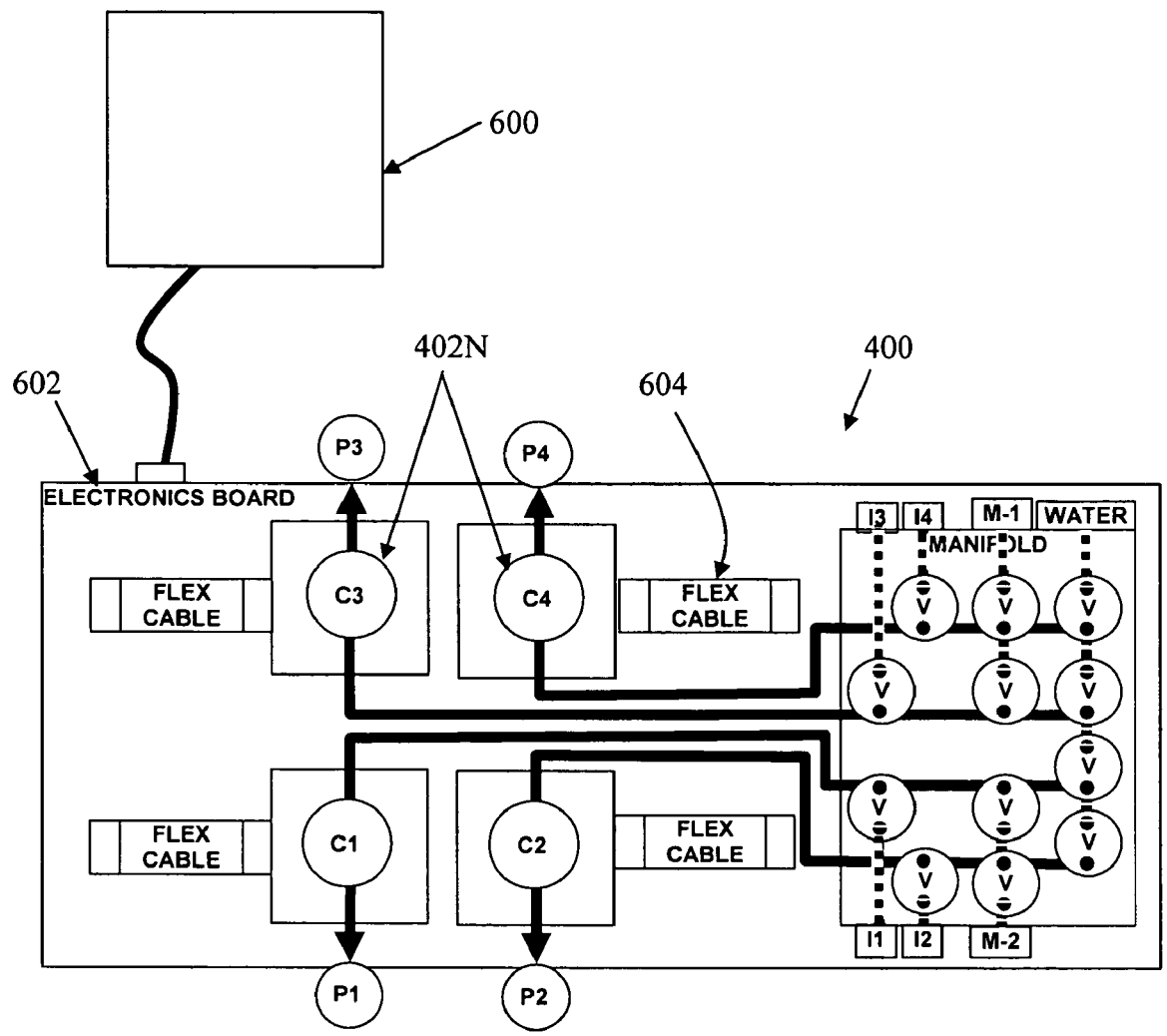
FIG. 6 is a block diagram of combinatrics and a microfluidics system according to the present invention, illustrating the electro-active species detection and observation apparatus being connected with a monitoring/analysis apparatus.

FIG. 6 is a block diagram of combinatrics and a microfluidics system according to the present invention, illustrating the electro-active species detection and observation apparatus 400 being connected with a monitoring/analysis apparatus 600. As shown in FIG. 6, a monitoring/analysis apparatus 600, such as a computer, may be connected with circuitry 602, which may thereafter be connected with any electro-active sensors inserted within the sealable chambers 402N. In one aspect, each sensor has its own dedicated electronics with circuitry and can be individually controlled.

Through use of the circuitry 602 and monitoring/analyzing apparatus 600, properties of the detection and observation apparatus 400 and any inserted electro-active sensors may be controlled and monitored. The circuitry 602 may be any suitable circuitry, a non-limiting example of which includes a dual mode circuitry as is further described below.

(6) Circuitry for Attaching with an Electro-Active Sensor

Figure 7A:
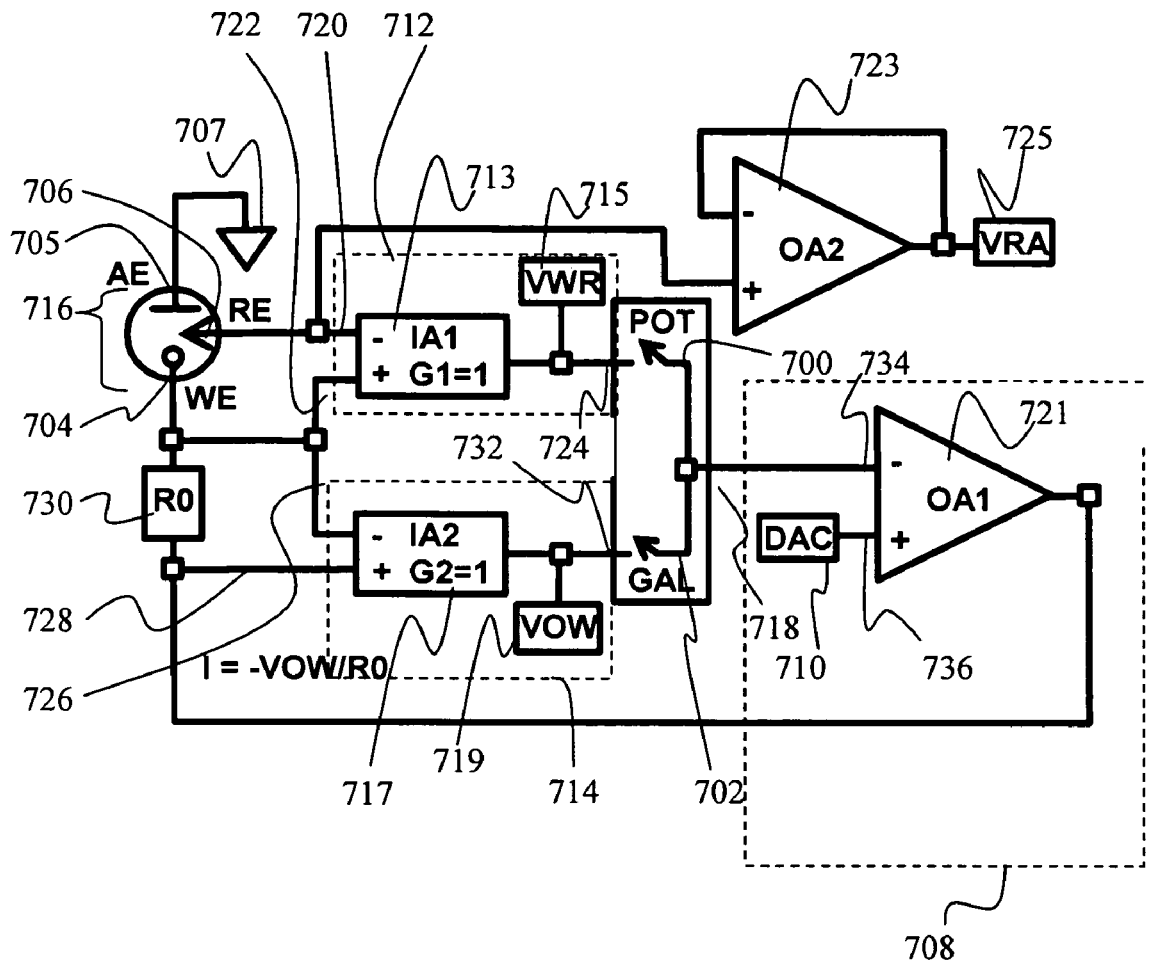
FIG. 7A is a circuit diagram depicting an aspect of the present invention, illustrating a potentiostat/galvanostat switch.
Figure 7B:
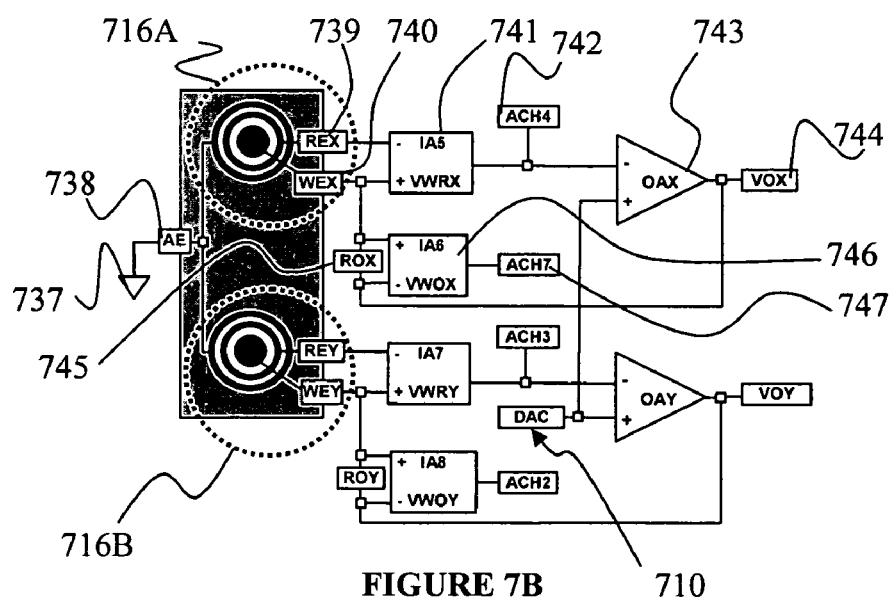
FIG. 7B is a circuit diagram depicting an aspect of the present invention illustrating circuitry incorporating two electrochemical cells.
Figure 7C:
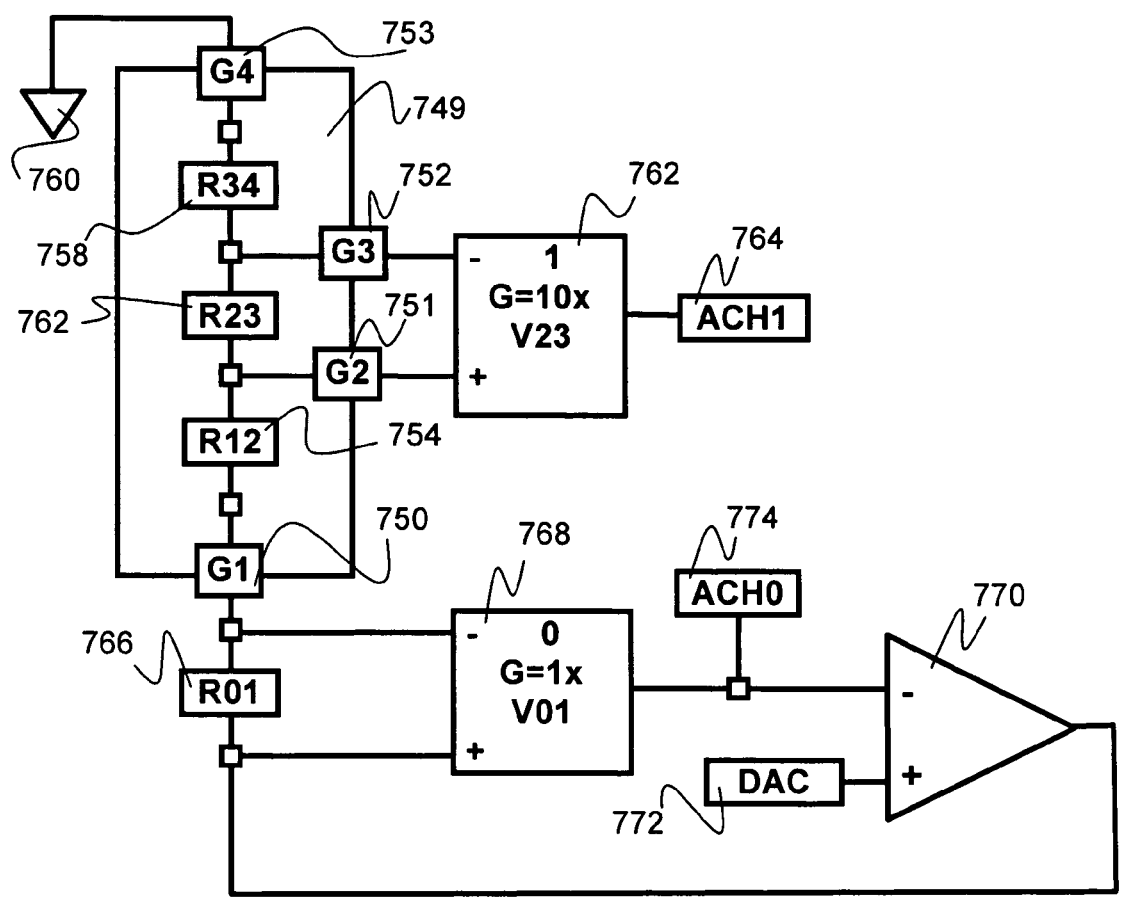
FIG. 7C is a circuit diagram depicting an aspect of the present invention, illustrating circuitry for a conductivity sensor.

Non-limiting examples of electronics used to measure the electro-active sensors 108, 124, and 126 of FIG. 1A, are shown in FIGS. 7A, 7B, and 7C. The redox cells and conductivity sensor can be measured in the potentiostat mode, where potential is forced and the current measured, or the galvanostat mode, where current is forced and the voltage measured. Switching between modes is controlled by an electronic switch. In some applications, it was found desirable to turn off unwanted cells by configuring them in the galvanostat mode with zero current, thereby preventing unwanted deposition of ionic species onto the electrodes.

The circuitry, shown in FIG. 7A, can be configure as a potentiostat 700 or a galvanostat 702. In the potentiostat 700 mode, a voltage difference is imposed between the working electrode (WE) 704 and the reference electrode (RE) 706 and the feedback circuit 708 adjusts the current accordingly. In the galvanostat 702 mode the current is forced through the cell 716, from the WE 704 to the auxiliary electrode (AE) 705, and the voltage between the WE 704 and the RE 706 adjusts accordingly. In one aspect, the AE is tied to ground 707. The dual-mode configuration is accomplished by the switch 718 shown in FIG. 7A. The circuitry is controlled by the DAC 710 (Digital-to-Analog-Converter). In one aspect and as shown in FIG. 7B, each cell 716A, 716B has it own circuit so that the cells can be operated independently of each other. The galvanostat 702 mode is useful in putting the cells in an off state, where the circuitry is placed in the galvanostat 702 mode and the current is set to zero. In this case no deposition occurs on the cell 716.

As shown in FIG. 7A, the dual mode circuitry comprises a potentiostat circuit portion 712 and a galvanostat circuit portion 714. The potentiostat circuit portion 712 and the galvanostat circuit portion 714 are connected with the electrochemical cell 716 and a switch 718. The switch 718 enables the dual mode circuitry to activate either the potentiostat 700, and 712 circuitry or the galvanostat 702, 714 circuitry. Further, the dual mode circuitry comprises a feedback circuit portion 708, which, when the potentiostat 700, 712 circuitry is activated, will impose a voltage difference between the WE 704 and the RE 706, and when the galvanostat 702, 714 circuitry is activated, will force a current through the electrochemical cell 716.

In one aspect, the potentiostat circuit portion 712 comprises a first instrumental amplifier (IA1) 713 having a gain of one and two inputs. A first input 720 is connected with the RE 706 and a second input 722 is connected with the WE 704. An output 724 of the potentiostat circuit portion 712 is connected with the switch 718. The voltage at the output 724 of the potentiostat circuit portion, measured at the point VWR 715, is equal to a difference between the voltages at the RE 706 and WE 704.

In one aspect, the galvanostat circuit portion 714 comprises a second instrumental amplifier (IA2) 717 having a gain of one and two inputs. A first galvanostat input 726 connected with the WE 704 and a second galvanostat input 728 connected with the WE 704 through a resistor 730. The resistor 730 allows for a calculation of the current flowing through the cell 716, whereby the current is equal to the voltage measured at a point VOW 719 divided by the resistance value of the resistor 730. An output 732 of the galvanostat circuit portion 714 is connected with the switch 718. The voltage at the output of the galvanostat circuit portion 714, measured at the point VOW 719, is equal to the voltage drop across the resistor 730.

In one aspect, the feedback circuit portion 708 comprises an operational amplifier (OA1) 721 with two inputs. A first input 734 connected with the switch 718 and a second input 736 connected with the DAC 710. An output of the feedback circuit 708 is connected with the WE 704. The DAC 710 allows for control of either the current through the cell 716 or the voltage difference imposed between the RE 706 and the WE 704.

In one aspect, the circuitry shown in FIG. 7A also comprises a second operational amplifier (OA2) 723 configured as a voltage follower. One input of OA2 73 is connected with the RE 706. The output of OA2 provides a voltage measurement at point VRA 725 of the voltage at RE 706.

Redox sensor circuitry shown in FIG. 7B is a dual potentiostat. Accordingly, each redox sensor 716A, 716B is driven from a common Digital-to-Analog-Converter (DAC) 710 but the current through the two redox sensors is measured independently. In practice it was found that the current and voltages through both devices were most often within a few percent of each other.

In one aspect, the dual potentiostat circuitry is configured as shown in FIG. 7B. In FIG. 7B, two redox sensors 716A, 716B are depicted with their auxiliary electrodes (AE) 738 tied to ground 737. The remainder of the circuitry shown in FIG. 7B will be described with reference to the first potentiostat circuit connected with the top redox sensor 716A. One skilled in the art will appreciate that the circuitry connected with the bottom redox sensor 716B operates in the same fashion as the description of the circuitry attached with the top redox sensor 716A.

The potentiostat circuitry attached with the top redox sensor 716A comprises of a first instrumental amplifier (IA5) 741 having two inputs. One input is connected with a reference electrode (RE) 739 of the redox sensor 716A, while the second input is connected with the working electrode (WE) 740 of the redox sensor 716A. The output of IA5 is measured at a point ACH4 742 and provides a measurement of the difference between the voltages at the RE 739 and the WE 740. The output of IA5 is fed into an operational amplifier (OAX) 743. The second input of OAX 743 is connected with the DAC 710. The DAC 710 allows the voltage difference between the RE 739 and the WE 740 to be imposed to a specified level. The point VOX 744 provides a voltage measurement point at the output of OAX 743. The output of OAX 743 is fed into one input of a second instrumental amplifier (IA6) 746. The other input of the IA6 746 is connected with the WE 740. A resistor (ROX) 745 is connected across the inputs of IA6 746. The output of the IA6 746 is measured at a point ACH7 747. By measuring the voltage at the output of IA6 746 and dividing it by the known resistance of the resistor 745 the current through the cell 716A can be calculated.

Circuitry used in measuring a conductivity sensor is shown in FIG. 7C. It is configured as a galvanostat and is used to force a current through adjacent electrodes found in the conductivity sensor seen in FIG. 1. As shown in FIG. 7C, the circuitry is immersed in a solution 749 and comprises four electrodes, shown as G1 750, G2 751, G3 752, and G4 753, where R12 754 indicates the resistance caused by the solution 749 between electrodes G1 750 and G2 751. R23 756 indicates the resistance caused by the solution 749 between electrodes G2 751 and G3 752, and R34 758 represents the resistance caused by the solution 749 between electrodes G3 752 and G4 753. In this example, electrode G4 753 is tied to a ground 760. The circuitry also comprises a first instrumentation amplifier 762. Inputs of the first instrumentation amplifier 762 are connected with electrodes G2 751 and G3 752. In this example, the first instrumentation amplifier 762 has a gain of 10. An output of the instrumentation amplifier 762 provides an analog channel 764 for monitoring the difference in voltage between the electrodes G2 751 and G3 752.

Further, the circuitry in FIG. 7C comprises a resistor R01 766 and a second instrumentation amplifier 768. The resistor R01 766 is connected between the electrode G1 750 and an output of an operational amplifier 770. Inputs of the second instrumentation amplifier 768 may be connected with each side of the resistor R01 766. An output of the second instrumentation amplifier 768 provides one input to the operational amplifier 770, while a Digital to Analog Converter 772 (DAC) provides a second input to the operational amplifier 770. The DAC 772 is used to set the current forced through the adjacent electrodes G1 750, G2 751, G3 752 and G4 753 of the conductivity sensor. One skilled in the art will appreciate that setting the DAC 772 equal to a voltage measured at the output of the second instrumentation amplifier ACH0 774, will result in no current being provided to the electrodes G1 750, G2 751, G3 752 and G4 753. Further, in one example, the resistance for R01 766 is selected to be 100 kΩ, whereby the current forced through the adjacent electrodes G1 750, G2 751, G3 752, and G4 753 is calculated by dividing the voltage measured at the output of the second instrumentation amplifier ACH0 774 by the resistance of R01 766.

One feature of aforementioned designs, as illustrated in FIG. 7B, is the shared AE which is in common with both cells. This feature reduces the number of pins or wires from the sensor pair and reduces the wire count when the sensors are connected in large arrays. In addition, as a non-limiting example, when the AE is grounded this provides an intrinsic isolation of each sensor in that their electric fields do not interfere. Another advantage of a grounded AE is that it provides a ground plane for the entire cell that acts like an electrical shield that reduces noise. The common, grounded AE is one feature of this electrochemical cell design.

(7) Experimental Results

With its electrochemical cells and sensors, the Electroactive sensor may be utilized for a wide variety of applications. In order to better understand its functionality and uses, the following experiments were conducted using the Electroactive sensor. Experimentation was initially undertaken using a first electro-active sensor entitled "first sensor". Upon further development of the sensor, a "second sensor" was developed which resulted in further experimentation. The following experiments and results are for demonstrative purposes only and are not intended to limit the use and scope of invention described herein. Rather, these results are intended to assist the reader in obtaining a better qualitative understanding of the concepts presented herein.

A. First Sensor Experimental Results (i) Introduction

The experiments described herein include measurements taken from the redox sensors, pH sensors, and conductivity sensors using the first sensor. The redox sensors were characterized using Cyclic Voltammetry (CV) and Anodic Stripping Voltammetry (ASV), both of which are well known techniques.

This experimental effort utilized an electrochemical cell that included a plurality of prefabricated Ion Selective Electrodes, a conductivity sensor, a temperature sensor and an oxidation reduction potential sensor.

A goal of this effort was to develop long-life sensors for water quality measurements. A table of trace elements found in drinking water is presented in FIG. 8. The first column includes the name of the trace element, with each elements molecular weight shown in second column. The remaining columns reflect each elements respective allowable contamination limits given in milligrams/Liter (mg/L) and micro Moles (μM), along with their standard reduction potentials (E°).

Measurements in this application will be directed toward detecting target ions such as $K^+$ (340 mg/L), $Ca^{2+}$ (30 mg/L), $MG^{2+}$ (50 mg/L) and $Cl^-$ (200 mg/L) which represent some of the U.S. agency, National Aeronautic and Space Administration's (NASA's) Spacecraft Maximum Contaminant Levels (MCL) for potable water for International Space Station Alpha (ISSA).

Figures 8, 9:
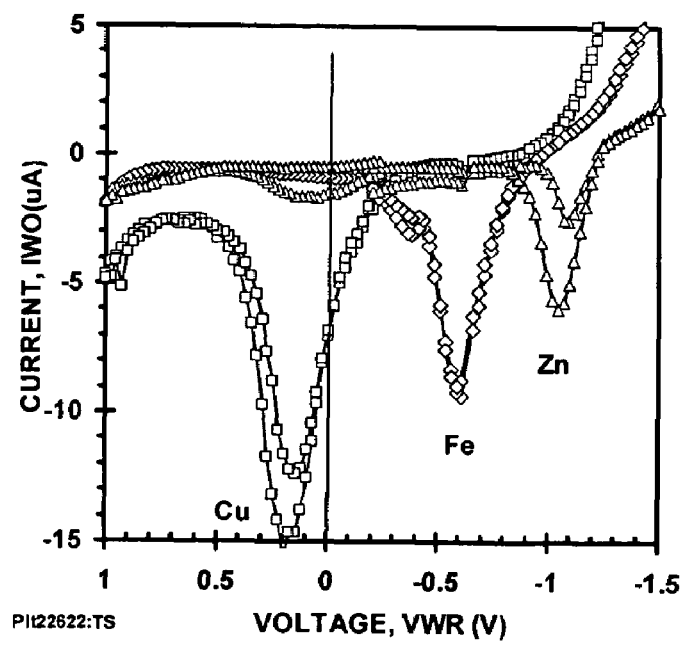
FIG. 8 is a table illustrating drinking water trace contaminants.
FIG. 9 is a graph illustrating ASV data for three heavy metals with 1 mM concentration, where the sweep rate was 100 mV/s, Tdep=5 s for $CuSO_4$, Tdep=100 s for $FeSO_4$, and Tdep=100 s for $ZnSO_4$.

Results obtained from electrochemical cells designed in accordance with the present invention and depicted in FIG. 1A, e.g. redox sensor, are shown in FIG. 9. FIG. 9 is a graph showing the results of an Anodic Stripping Voltammetry (ASV) experiment. In this graph, the X axis represents voltage in Volts (V), and the Y axis represents a current in micro Amps (uA).

Here the sensor was sequentially exposed to 1 milli Mole (mM) of $CuSO_4$, $FeSO_4$, and of $ZnSO_4$. The data was acquired using ASV, where the sweep rate was 100 mV/s, with Tdep=5 s for $CuSO_4$; Tdep=100 s for $FeSO_4$; and Tdep=100 s for $ZnSO_4$, at a deposition time of Tdep and at a scan rate of S. As shown in FIG. 9, two curves are shown for each ion to delineate repeatability issues. For data shown in FIG. 9, a negative potential of −1.5 V was applied to the working electrode (WE) for Tdep. The voltage was then scanned to +1 V and the ions depleted at a potential that is related to the ions' position in the Electrochemical Series. Thus, the possible chemical identity of an unknown ion can be tentatively determined by this technique. The tentative nature of the identification has to do with the lack of uniqueness of the redox potential. That is, there are a number of ions or molecules that can have the same potential.

(ii) Waveforms

In the measurements there were three waveforms that were sent through the Digital-to-Analog-Converter (DAC): Triangle Step Wave, Ramp Step Wave, and Ramp Square Wave. Each waveform is associated with a particular measurement method. The Triangle Step Wave is used with the Cyclic Voltammetry (CV) method, the Ramp Step Wave is used with the ASV method and termed ASVst. Finally, the Ramp Square Wave is used with ASV and termed ASVsq. Another method was also developed consisting of calculating the second derivative of the ASVst response and is termed D2ASVst.

Figure 10:
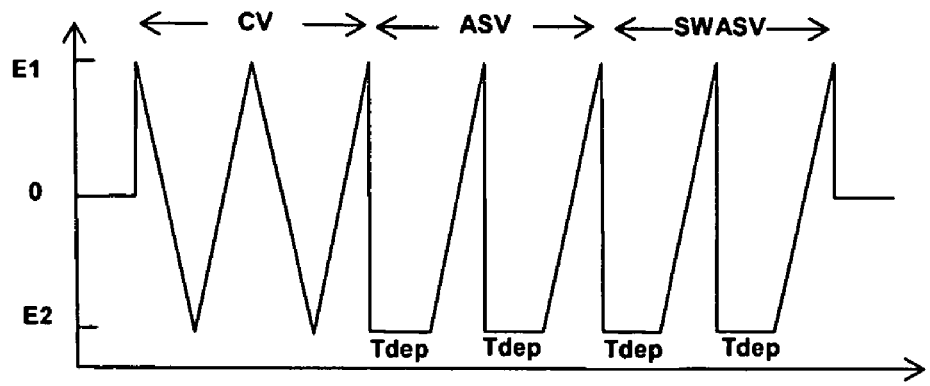
FIG. 10 is a plot of wave shapes for three measurement methods.

The wave shapes used in these measurements are shown as a plot graph in FIG. 10, where voltage peaks are labeled on the Y axis, with a positive voltage peak labeled as E1 and a negative voltage peak labeled as E2. The waves were created using a 12-bit DAC with a resolution of 2.5 mV. A total of 100 data points were taken between E1 and E2. For example, in a span (E1-E2) of 2 V, each step was 20 mV. For the square wave, a 100-mV peak-to-peak square wave was superimposed on the step wave. The difference in the currents measured on either side of the square wave was plotted in the ASVsq graphs. The measurements were conducted at a stated scan rate, S, and seven Tdep times which varied from 10 s to 1000 s in a 1, 2, 5 sequence. The overall measurement time was of the order of 4 hours.

(iii) Conductivity Measurements

The conductivity measurements utilized the circuitry seen in FIG. 7C. The conductivity was determined using an alternating current (AC) ramp triangle wave. It is well-known that conductivity cells cannot be measured using direct current (DC). This is due to the fact that the conducting carriers in solution are ions, not electrons. For conduction to occur ions must continually exchange electrons with an electrode through electrochemical oxidation or reduction and this requires an alternating current (AC).

In operation, an AC signal was generated using the DAC 772 seen in FIG. 7C. It produced a voltage triangle wave with a sweep rate of 1 V/s that was proportional to the current through the sensor. The circuitry produced a current ramp of 10 micro Amps/second (μA/s) through the sensor. Results, shown in FIG. 11 for a number of Hydro Chloric Acid (HCl) solutions, have a current span of ±1 μA. The results for pure water (SigmaPure H20lv4c14) are represented by the squares. The results for 10 μM (micro-molarity, wherein molarity is moles per liter of solution) of HCllv4c14sigmapure are represented by the diamonds. The results for 100 μM of HCllv4c14sigmapure are represented by the triangles. The results for 1000 μM of HCllv4c14sigmapure are represented by the ovals. As shown the zero-current intercept voltage was different for each electrolyte.

Figure 11:
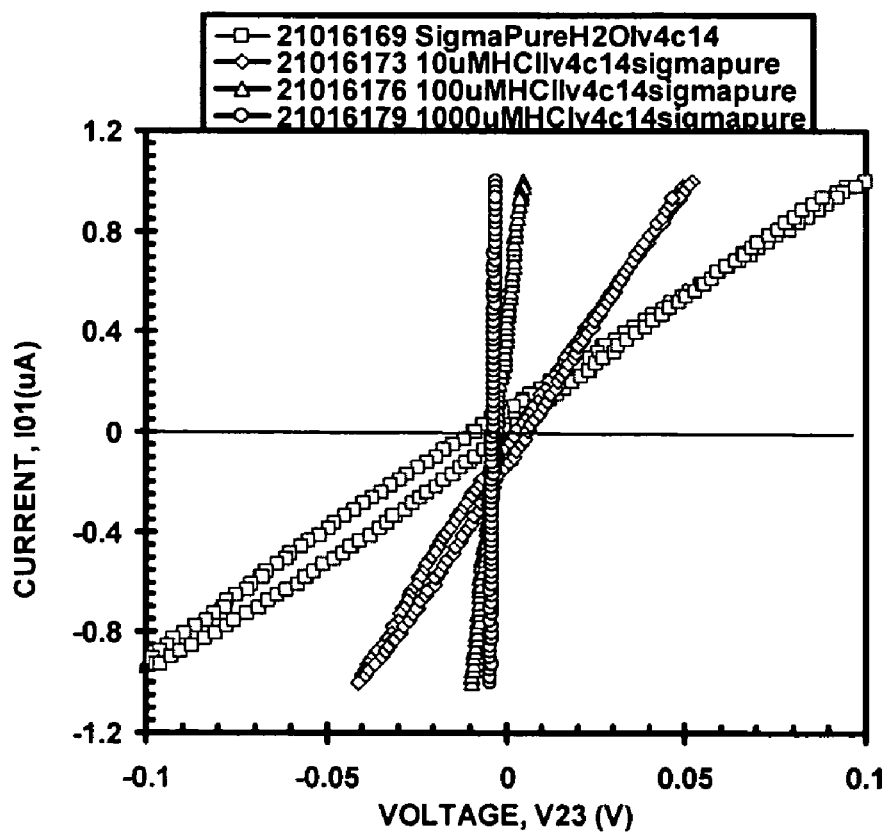
FIG. 11 is a graph illustrating a conductivity sensor response to pure water and three HCl solutions.

As previously discussed, the conductivity sensor may be turned off when not in use by specifying zero current. The zero-current condition forces the sensor to be in an electrochemically inactive state. An alternate approach is to drive the sensor with a potentiostat where the turn-off state is zero volts. As seen in FIG. 11, even at zero volts, significant currents flow in some cases and this can cause deposition of the electroactive species on the driven electrodes of the conductivity sensor.

The solution resistivity, $\rho(\Omega\text{-cm})$, was determined from the resistance, R, determined from the slope of the data seen in FIG. 11 using a least fitting squares technique. The resistivity for the four-probe conductivity sensor seen in FIG. 1A is assumed to follow:

$$\rho = G \cdot d \cdot R, \quad (1)$$

where d=0.125 cm is the distance between adjacent probes seen in FIG. 1 and the geometrical factor, G=10.726, a unitless constant. The actual results are shown as measured data points, RhoMeas, in FIG. 12, where the line between the points was produced by a least squares method.

Figure 12:
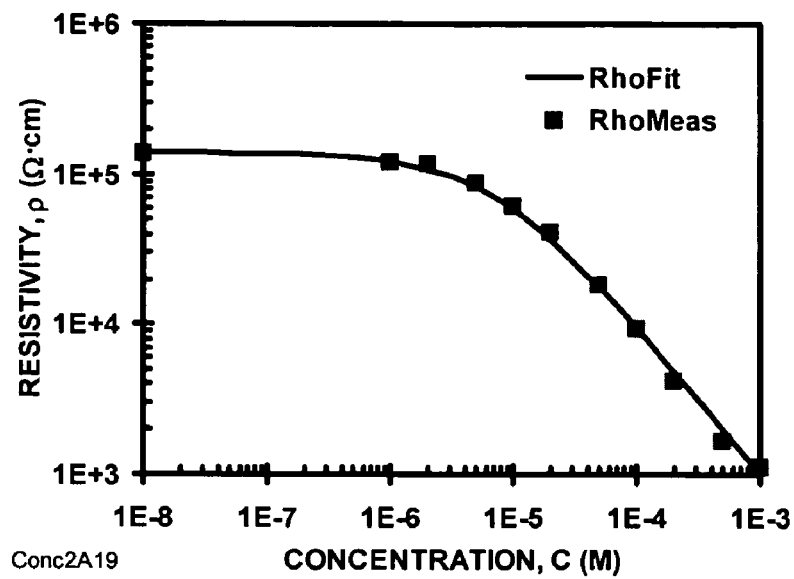
FIG. 12 is a graph illustrating a conductivity sensor HCl response.

A simple model was developed to fit the results seen in FIG. 12. Two resistors are placed in parallel. One resistor represents the clean water resistance, $R_o$ in Ohms ($\Omega$), and the other resistor represents the electrolyte resistance, $R_e$ in Ohms ($\Omega$) The total resistance, R in Ohms ($\Omega$), is:

$$R = \frac{R_0}{\left(1 + \frac{R_0}{R_e}\right)} \quad (2)$$

The water resistance is given by:

$$R_o = \rho_o / (10.726 \cdot d) \quad (3)$$

The electrolyte resistance $R_e$ ($\Omega$) was formulated from a combination of Equation 1, subscripted for the electrolyte, and the definition of the electrolyte resistivity $C_e$ (M):

$$\rho_e = 1000 (\lambda_e \cdot C_e) \quad (4)$$

where $\lambda_e$ ($cm^2/(\Omega \cdot mol)$) is the electrolyte's equivalent ionic conductivity. The combination of equations yields:

$$R_e = \frac{1000}{10.726 \cdot d \cdot \lambda_e \cdot C_e} \quad (5)$$

Substituting Eqs. 1, 3 and 5 into Eq. 2 and rearranging yields the fitting equation:

$$\rho = \frac{\rho_o}{1 + \left(\frac{\rho_o \cdot \lambda_e}{1000}\right) C_e} \quad (6)$$

The result of the curve fitting process yields $\rho_o = 140 \, k\Omega \cdot cm$ and $\lambda_e = 988 \, cm^2/(\Omega \cdot mol)$. The resistivity of clean water should be near 18 $M\Omega \cdot cm$ (megaohms·centimeter) so the low value for $\rho_o$ indicates that the water contains residual contamination. The formal value for $\lambda_e$ is 421 $cm^2/(\Omega \cdot mol)$ at 1 mM (milli-molarity). Both extracted values are sensitive to the G·d product. Further investigations are directed at determining a suitable value for the G·d product to allow quantitative measurements.

(iv) CV Measurements

Figure 13:
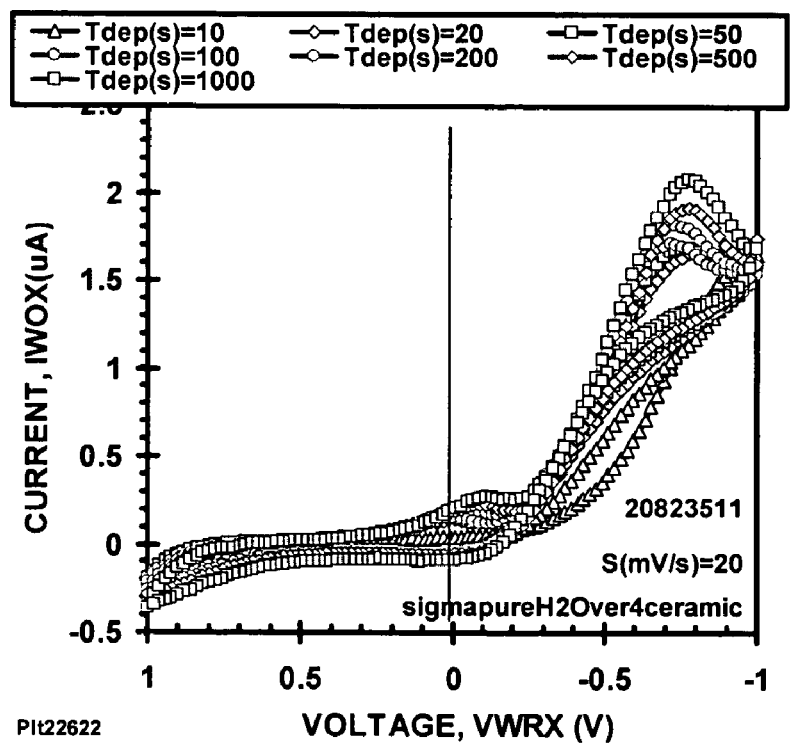
FIG. 13 is a graph illustrating a Cyclic Voltammetry (CV) response for Sigmapure water.

The CV method provides a survey of high-concentration species in solution. An example is seen in FIG. 13 for clean water. In the disclosed example, this curve is acquired seven times, once after each deposition time (Tdep) cycle. In principle the set of curves should be independent of the Tdep and provides insight into the stability of the solution over the four-hour measurement cycle. This wave shape was unique to the first sensor electrodes where all three electrodes, AE, WE, and RE were planar. The peaks that appear at −0.1 and −0.75 V grow with Tdep and were tentatively attributed to the accumulation of oxygen or carbon dioxide in the sample chamber. This observation was consistent with the conductivity sensor measurements that indicated that the sample chamber contained residual contamination.

(v) ASV Measurement Conditions

The ASV measurement provides a method of accumulating ions on the WE and thus this method is known to have sensitivities in the pM (pico-Molarity) range. The operating conditions for the ASV method are well described by the data presented in FIG. 14. This data was acquired from 100 μM (micro-Molarity) $CuSO_4$ and was scanned at four different rates, FIGS. 14A, 14B, 14C and 14D, and for seven deposition times, each deposition time being represented by a set of points on FIGS. 14A-14D.

Figure 14A:
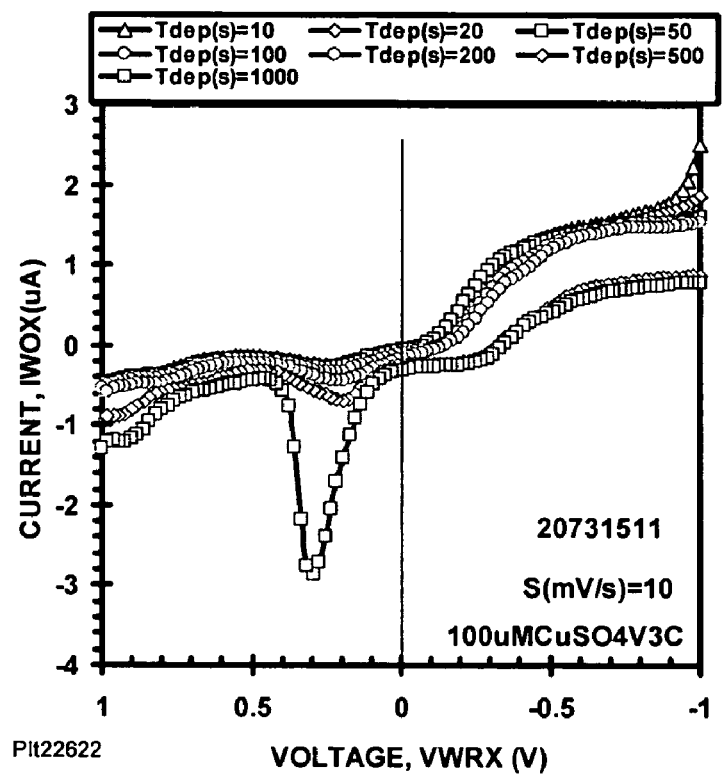
FIG. 14A is a graph illustrating a measured Anodic Stripping Voltammetry curve (ASVst) response for 100 micro mole ($\mu M$) $CuSO_4$ scanned at 10 mV/s.

FIG. 14A depicts the ASV measurement for 100 μM (micro-Molarity) $CuSO_4$ scanned at a rate of S=10 milivolts per second. The seven deposition times are depicted in the Figure. The line represented by the squares occurred at a deposition time of 50 seconds. The line represented by the triangles occurred at a deposition time of 10 seconds. Other deposition times include 20, 100, 200, 500 and 1000 seconds.

FIG. 14B depicts the ASV measurement for 100 μM (micro-Molarity) $CuSO_4$ scanned at a rate of S=20 milivolts per second. The seven deposition times are depicted in the Figure. The line represented by the squares occurred at a deposition time of 50 seconds. The line represented by the triangles occurred at a deposition time of 10 seconds. Other deposition times include 20, 100, 200, 500 and 1000 seconds.

Figure 14:
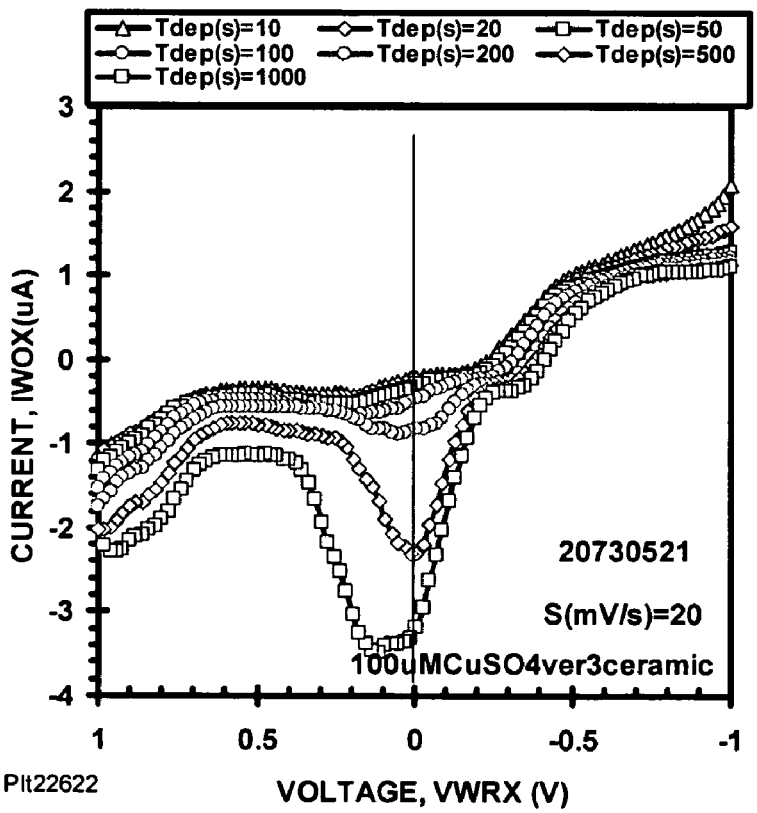
FIG. 14B is a graph illustrating an ASVst response for 100 $\mu M$ $CuCO_4$ scanned at 20 mV/s.
FIG. 14C is a graph illustrating an ASVst response for 100 $\mu M$ $CuCO_4$ scanned at 50 mV/s.
FIG. 14D is a graph illustrating an ASVst response for 100 $\mu M$ $CuCO_4$ scanned at 100 mV/s.
Figure 14C:
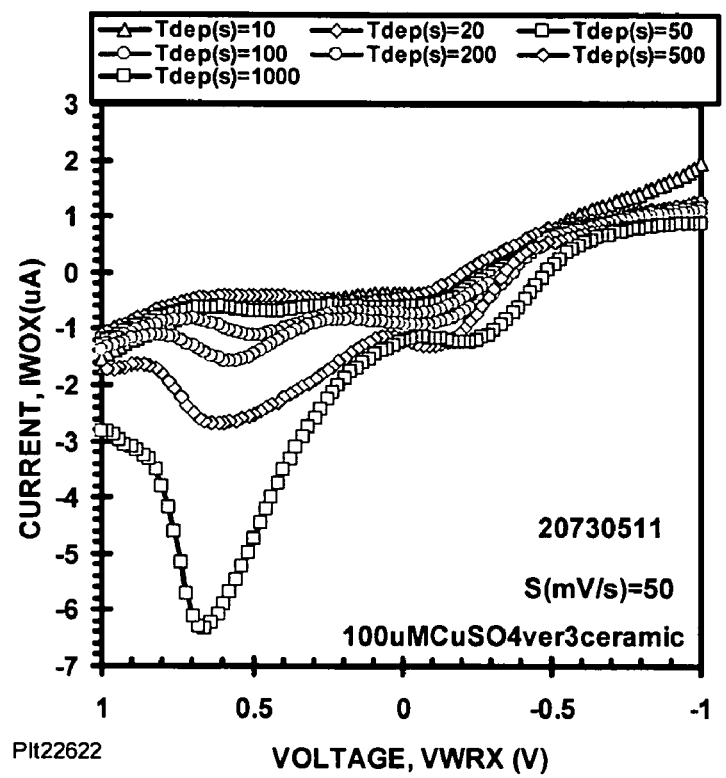

FIG. 14C depicts the ASV measurement for 100 μM (micro-Molarity) $CuSO_4$ scanned at a rate of S=50 milivolts per second. The seven deposition times are depicted in the Figure. The line represented by the squares occurred at a deposition time of 50 seconds. The line represented by the triangles occurred at a deposition time of 10 seconds. Other deposition times include 20, 100, 200, 500 and 1000 seconds.

Figure 14D:
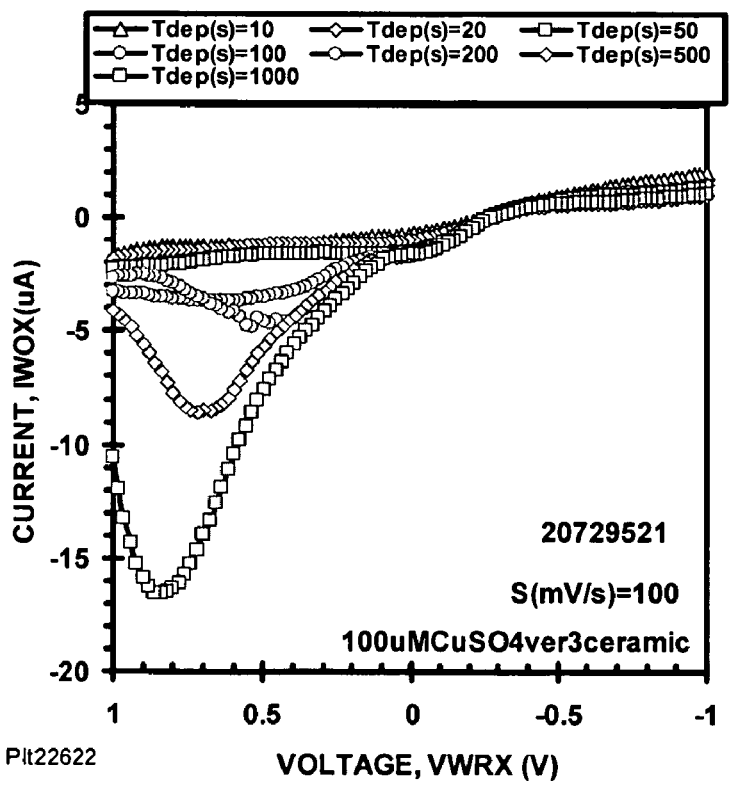

FIG. 14D depicts the ASV measurement for 100 μM (micro-Molarity) $CuSO_4$ scanned at a rate of S=100 milivolts per second. The seven deposition times are depicted in the Figure. The line represented by the squares occurred at a deposition time of 50 seconds. The line represented by the triangles occurred at a deposition time of 10 seconds. Other deposition times include 20, 100, 200, 500 and 1000 seconds.

Figure 15A:
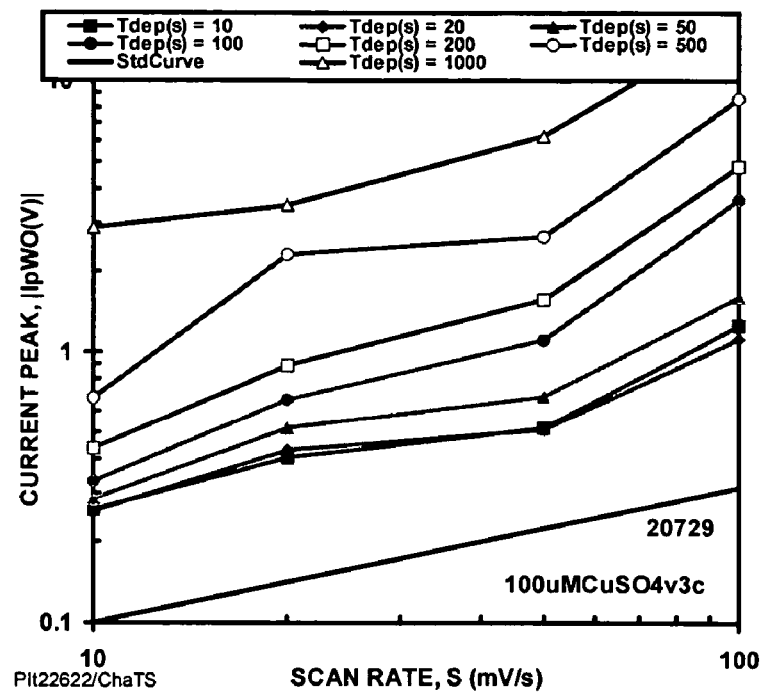
FIG. 15A is a graph illustrating an analysis of data shown in FIG. 14, showing the dependence of a current peak on a square root of a scan rate.
Figure 15B:
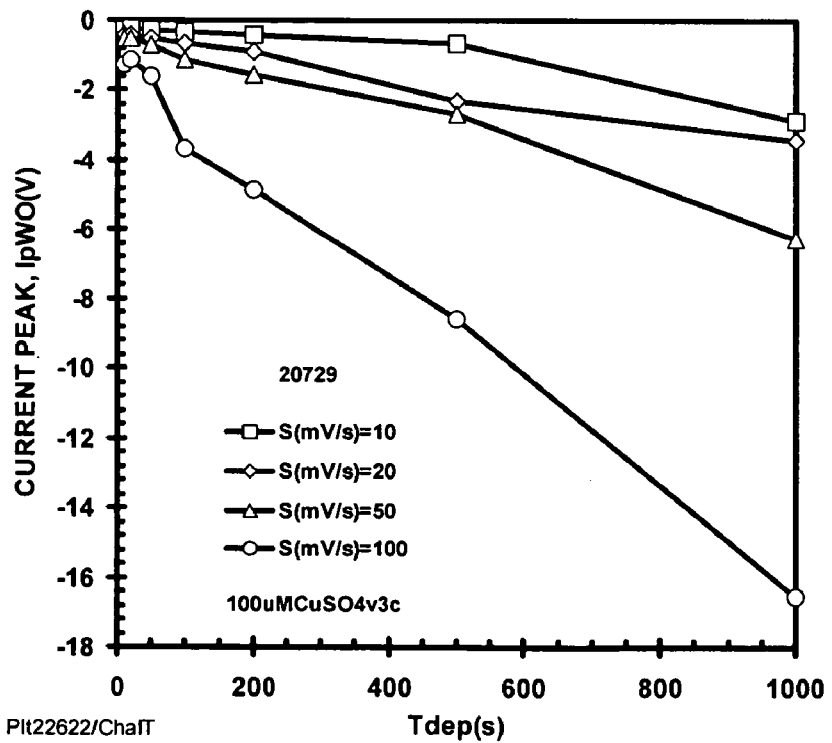
FIG. 15B is a graph illustrating an analysis of data shown in FIG. 14, showing a linear dependence of the current peak on deposition time.

The ASV method begins with a deposition time, Tdep. Referring to the voltage waveform, seen in FIG. 10, the voltage scan starts at the most negative voltage, E2, and proceeds to the most positive voltage, E1, at a linear scan rate of S. The process is repeated twice in order to observe the stability of the measurement. Most of the time the second trace overlaps the first trace. Except for the data seen in FIG. 9, the results reported are for the second trace. The peak currents are plotted in FIG. 15A as a function of scan rate and in FIG. 15B as a function of deposition time. The effect of the scan rate on the current peak height, IpWO, is seen in FIG. 15A. The data generally has a slope of 0.5 on the log-log plot. The behavior of the slope and the fact that the voltage peak is scan rate dependent as seen in FIG. 14 leads to the choice of the totally irreversible system to explain this behavior:

$$Ip = 2.99 \cdot 10^5 \cdot \alpha^{1/2} \cdot A \cdot D^{1/2} \cdot C \cdot S^{1/2} \qquad (7)$$

where $\alpha$ is the transfer coefficient, A the area of the WE, D the diffusion coefficient, C the concentration of the electro-active species, and S the scan rate. The data in FIG. 15B proves an indication that the deposition time, Tdep, is a linear function that is proportional to concentration. This linear behavior on concentration is also described by Eq. 7.

Operating principles for ASV measurements are summarized as follows:

a. Larger peak currents occur at higher Tdep and S values. This is an important consideration when attempting to measure trace amounts of ionic species.

b. The penalty for operating at higher Tdep and S values is that the peak voltage shifts toward more positive voltages. In addition the ASV base-line slope increases due to the double-layer capacitance.

(vi) ASV Experiments

The value of the ASV technique is found in its ability to detect low-concentrations of ionic species in solution, to provide probable identities for the electro-active species from their redox potentials, and to quantify the concentration of species. In this experiment, the focus is on determining the redox potential by extrapolating peak current-voltage values to zero current. ASV results were obtained from $PbCL_2$ shown in FIG. 16, from $ZnSO_4$ shown in FIG. 17, from $CuSO_4$ shown in FIG. 18, and from NaCl shown in FIG. 19. The results presented in the following order: (a) measured ASV curves (ASVst), (b) calculated second derivative curves (D2ASVst), and (c) peak current-voltage curves.

From an analysis of the D2ASVst plot, the peak current-voltage was determined at each Tdep value and use to form the peak current-voltage curve. This curve is used to determine $E_o$ values by extrapolating the peak current-voltage curve to zero current. In order to determine the peak curve, the second derivative of the ASVst data was calculated and shown in the D2ASVst plot.

The second derivative is well-known in spectroscopy for identifying the location of peaks and for being able to identify shoulder peaks where two peaks are very close to each other. The second derivative of the ASVst response is determined by fitting a second-order polynomial to the ASVst data using a five-point least-squares fitting method. This was implemented in Excel using the LINEST function. Results are shown in FIGS. 16b, 17b, 18b, and 19b.

Concerning the D2ASVst curves seen in FIG. 16a, 17a, 18a, and 19a, three observations are in order: First, the base-line drift due to double-layer charging has been removed. Second, the second derivative has a significant negative going feature that is due to the lack of symmetry in the ASVst response. Third, the second derivative is a good method for identifying the location of peaks.

Figure 16A:
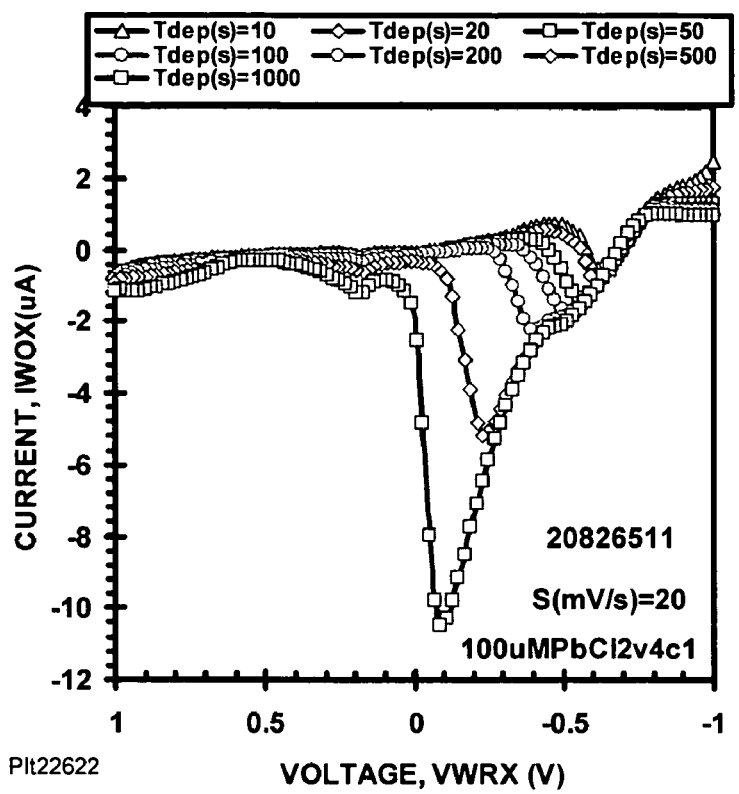
FIG. 16A is a graph illustrating an ASVst response for 100 $\mu M$ $PbCl_2$.
Figure 16B:
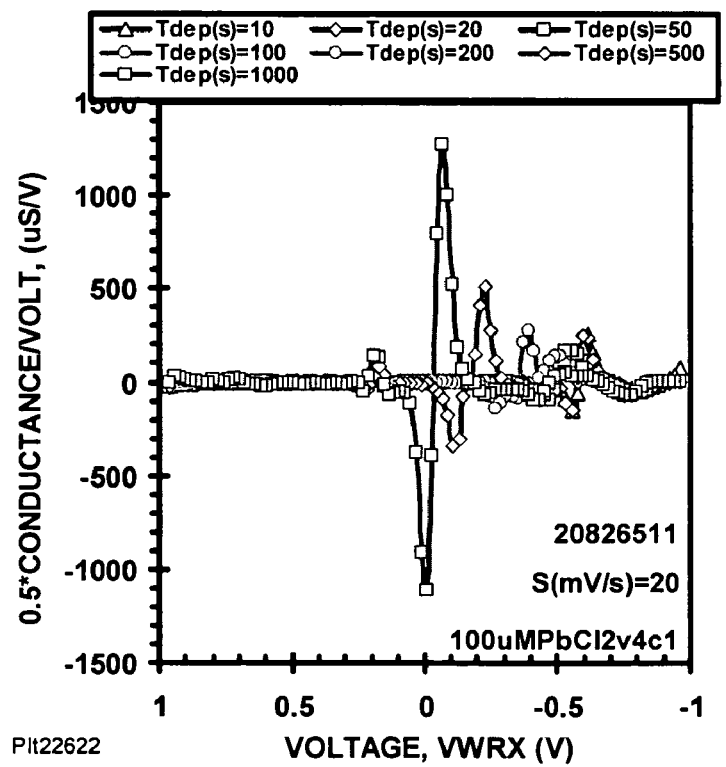
FIG. 16B is a graph illustrating a calculated second derivative curve (D2ASVst) response for 100 $\mu M$ $PbCl_2$ data shown in FIG. 16A.
Figure 16C:
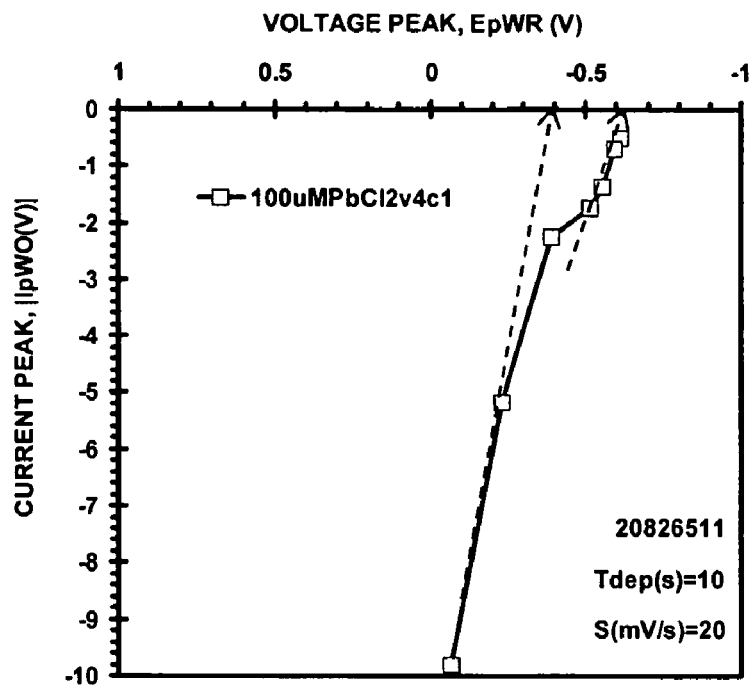
FIG. 16C is a graph illustrating ASV peak values derived from the 100 $\mu M$ $PbCl_2$ data seen in FIG. 16A, where $E_{po}4=-0.40V$ and $E_{po}5=-0.65V$.
Figure 17A:
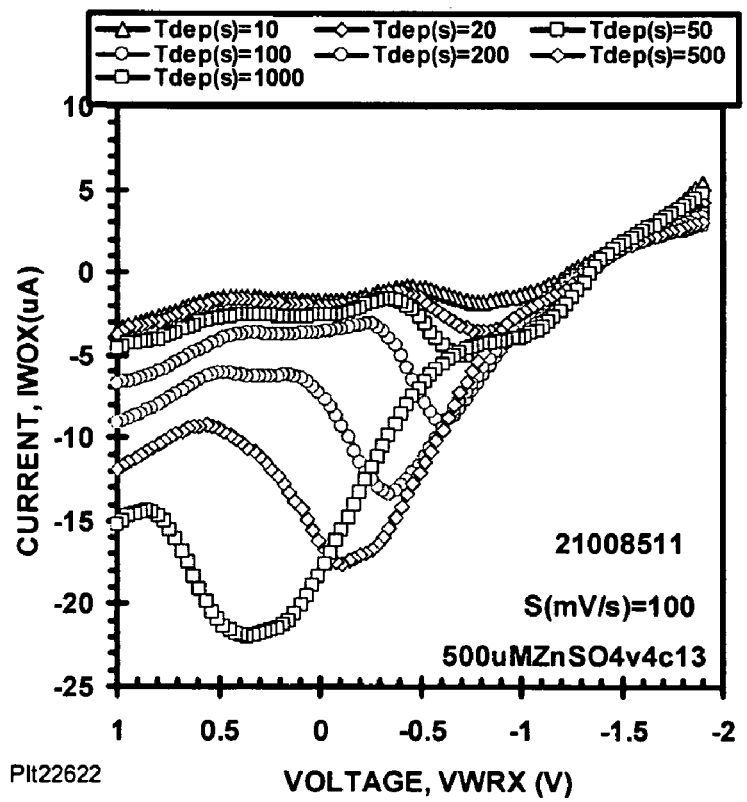
FIG. 17A is a graph illustrating an ASVst response for 500 $\mu M$ $ZnSO_4$.
Figure 17B:
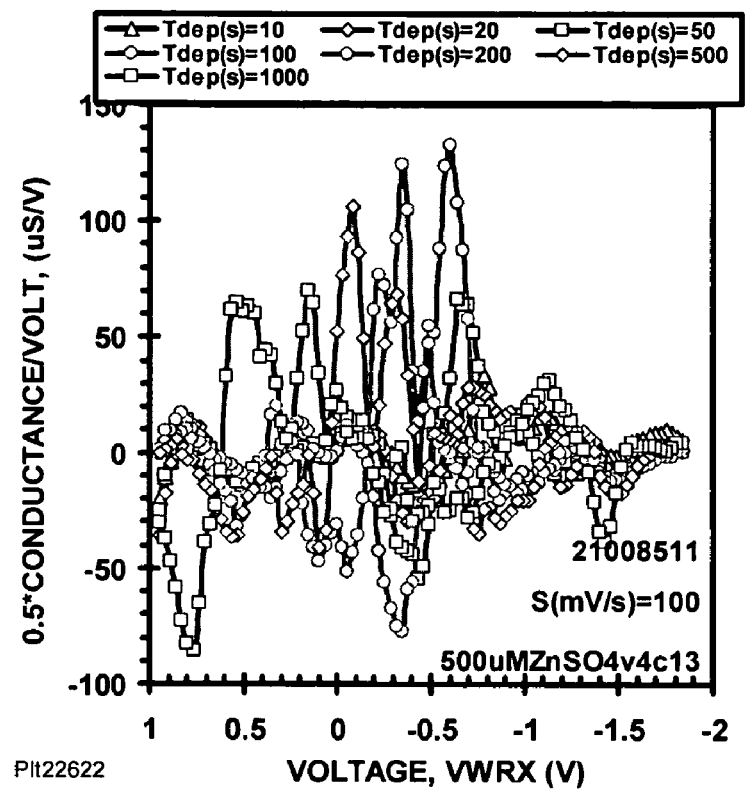
FIG. 17B is a graph illustrating a D2ASVst response for 500 $\mu M$ $ZnSO_4$ data shown in FIG. 17A.
Figure 17C:
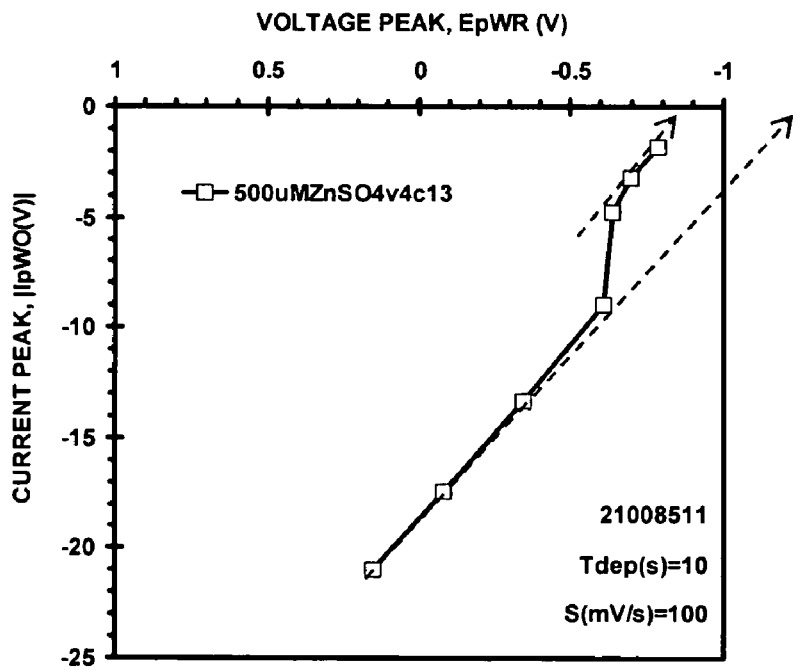
FIG. 17C is a graph illustrating ASV peak values derived from the 500 $\mu M$ $ZnSO_4$ data shown in FIG. 17A, where $E_{po}6=-0.80V$ and $E_{po}7=-1.25V$.
Figure 18A:
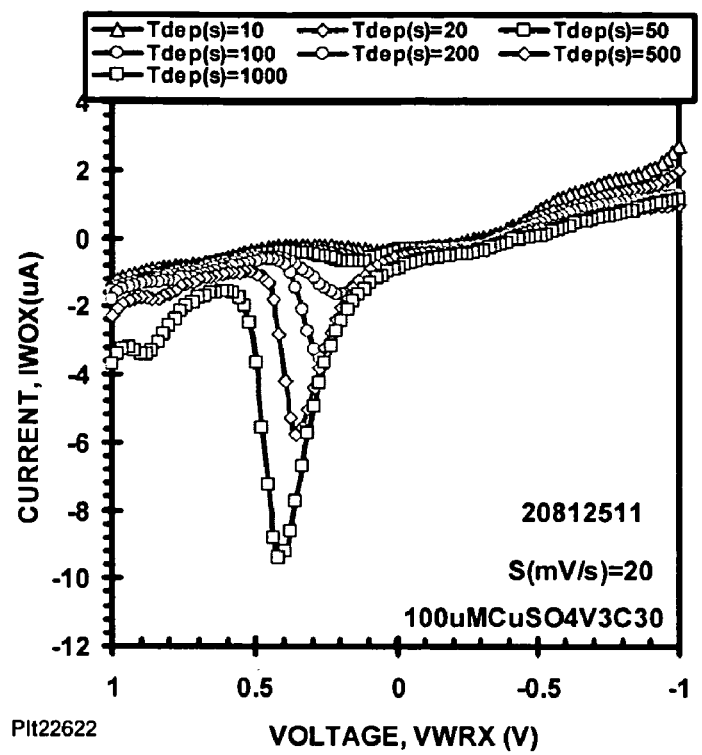
FIG. 18A is a graph illustrating an ASVst response for 100 $\mu M$ $CuSO_4$.
Figure 18B:
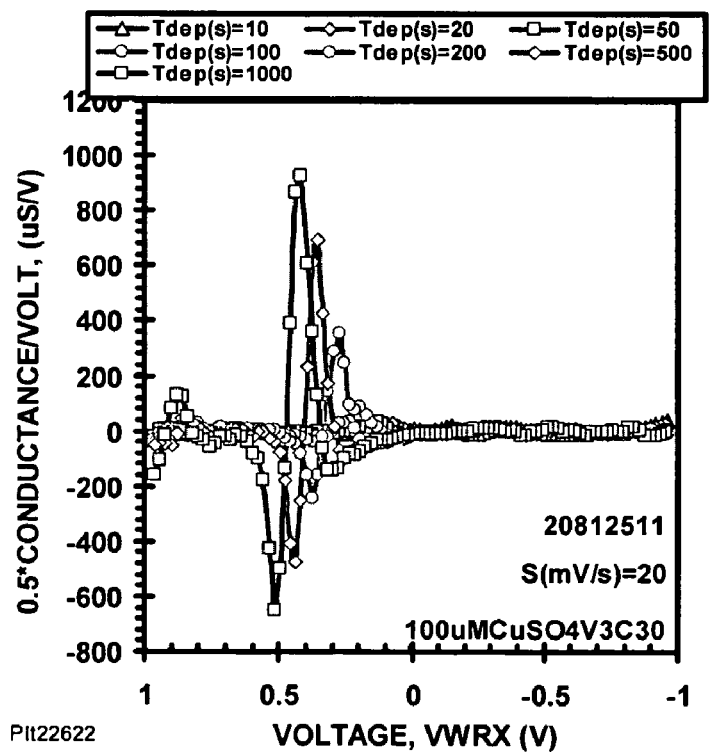
FIG. 18B is a graph illustrating a D2ASVst response for 100 $\mu M$ $CuSO_4$ data shown in FIG. 18A.
Figure 18C:
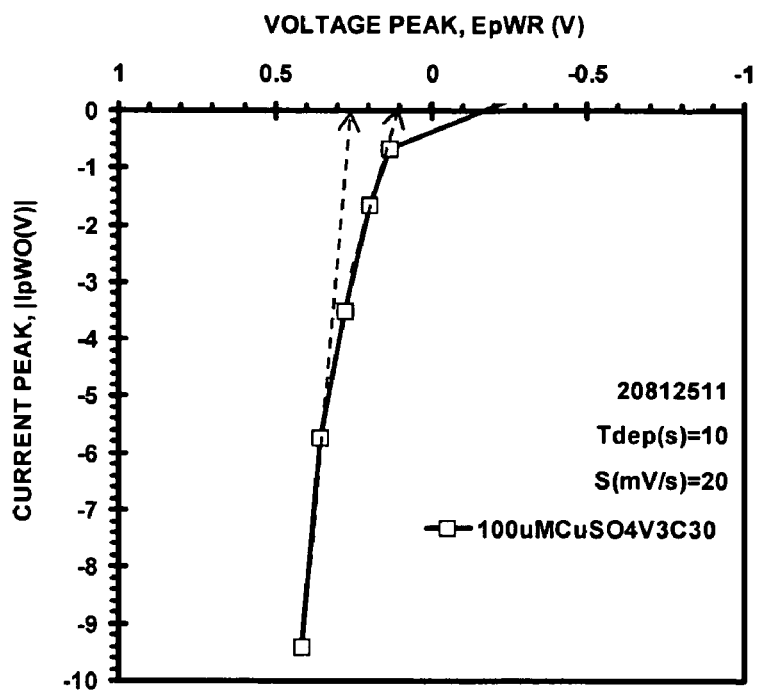
FIG. 18C is a graph illustrating ASV peak values derived from the 100 $\mu M$ $CuSO_4$ data shown in FIG. 18A, where $E_{po}1=+0.26$ and $E_{po}2=+0.09V$.

The extraction of the peak currents and voltages was implemented in an Excel macro designed to sort the data and find the peak values. The results are shown in FIGS. 16c, 17c, 18c, and 19c. The data clearly shows that two species are being oxidized as seen in FIGS. 16, 17, and 18. This is most evident in the ASVst curve seen in FIG. 16a for PbCl2 and in the peak plot seen in FIG. 17c for $ZnSO_4$.

Figure 19A:
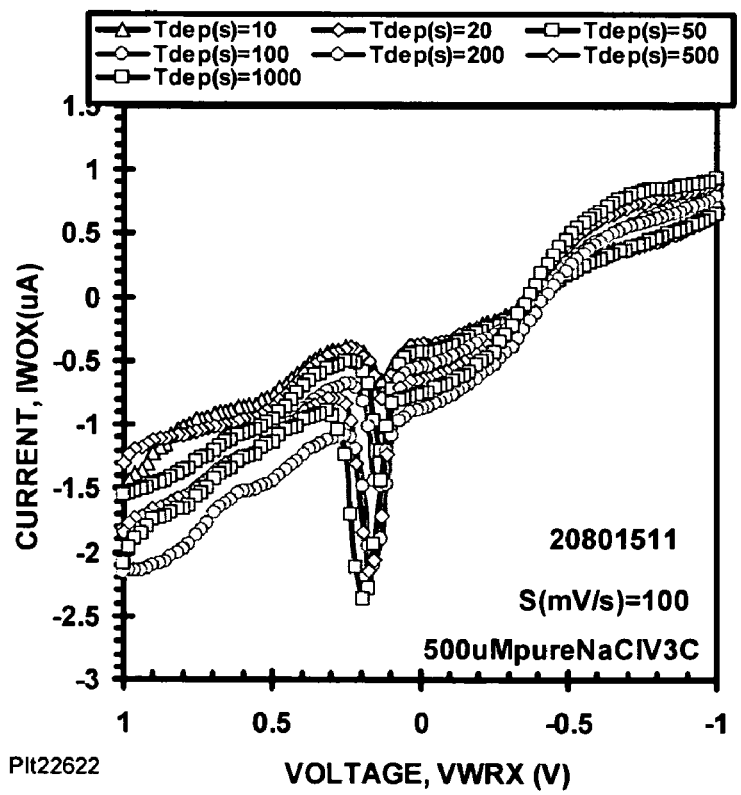
FIG. 19A is a graph illustrating an ASVst response for 500 $\mu M$ NaCl.

The results for the NaCl differ from the others. First, the peak current-voltage plot seen in FIG. 19c shows that the peak voltage does not vary with Tdep. This is suggestive of a totally reversible system. A possible explanation is that chlorine is reacting with the Ag RE and forming AgCl. The voltage independence on Tdep suggests that it might be used as a calibrator ion when relating results to reduction potentials, $E°$ listed in the Electrochemical Series [HCP].

Figure 19B:
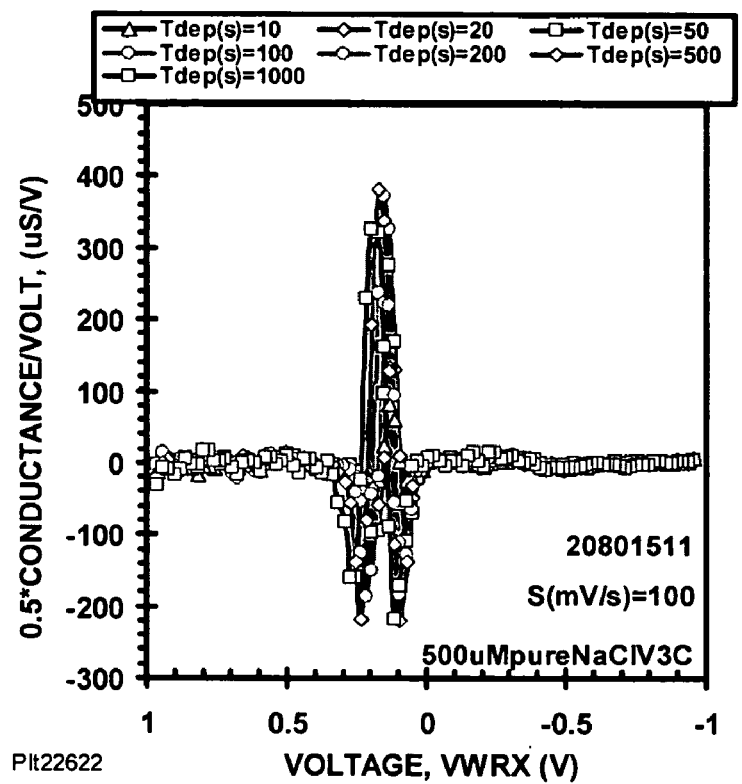
FIG. 19B is a graph illustrating a D2ASVst response for 500 $\mu M$ NaCl data shown in FIG. 19A.
Figure 19C:
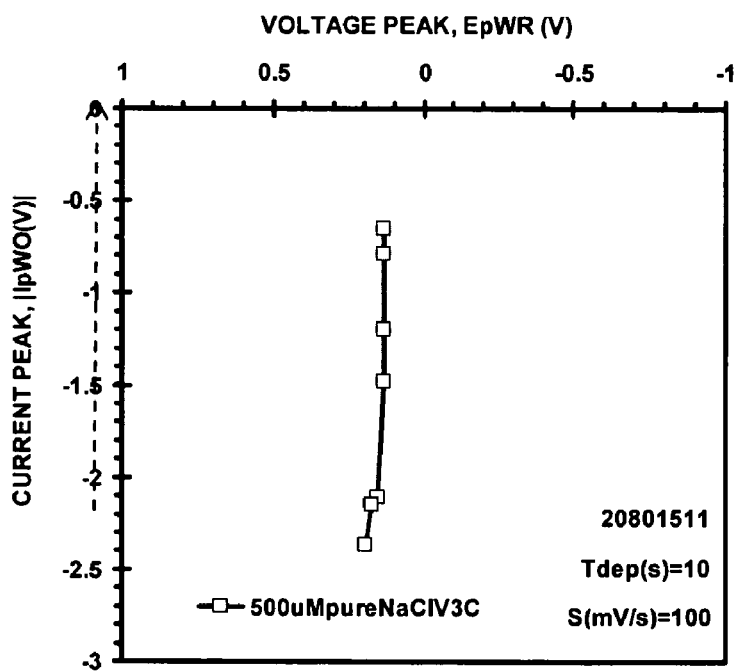
FIG. 19C is a graph illustrating ASV peak values derived from the 500 $\mu M$ NaCl data shown in FIG. 19A, where $E_{po}3=+0.133$ V.

Another NaCl observation can be gleaned from the second derivative curves seen in FIG. 19b. They indicate that the ASV response curves seen in FIG. 19a are symmetrical. The symmetry of the NaCl ASV response is not shared by Pb, Zn, and Cu curves. Their second derivative curves are not symmetrical. These observations are key to understanding the nature of the interaction of the electroactive species with the WE.

(vii) ASV Analysis

In this section the peak current-voltage curves seen in FIGS. 16C, 17C, 18C and 19C are analyzed for possible reactions. For the oxidation of a totally reversible system, the ASV peak current-voltage relation is modeled by:

$$I_\rho = -|I_{\rho o}| \exp[(1-\alpha) \cdot f(E_\rho - E°)] \quad (8)$$

where $\alpha$ is the transfer coefficient and $f=38.92\,V^{-1}$ at 25° C. As seen in FIGS. 16C, 17C, 18C and 19C, the peak current-voltage relationship is linear. Linearizing Eq. 8, assuming the exponent is small, leads to:

$$I_\rho = -|I_{\rho o}|[1+(1-\alpha) \cdot f(E_\rho - E_o)] \quad (9)$$

where $E_o$ is the experimentally determined reduction potential. To determine $E_o$, $I_\rho$ is set to zero in Eq. 9 which results in the following:

$$E_o = E_{\rho o} + 1/[(1-\alpha) \cdot f] \quad (10)$$

where $E_{\rho o}$ is the $I_\rho = 0$ intercept value.

Figures 20, 21:
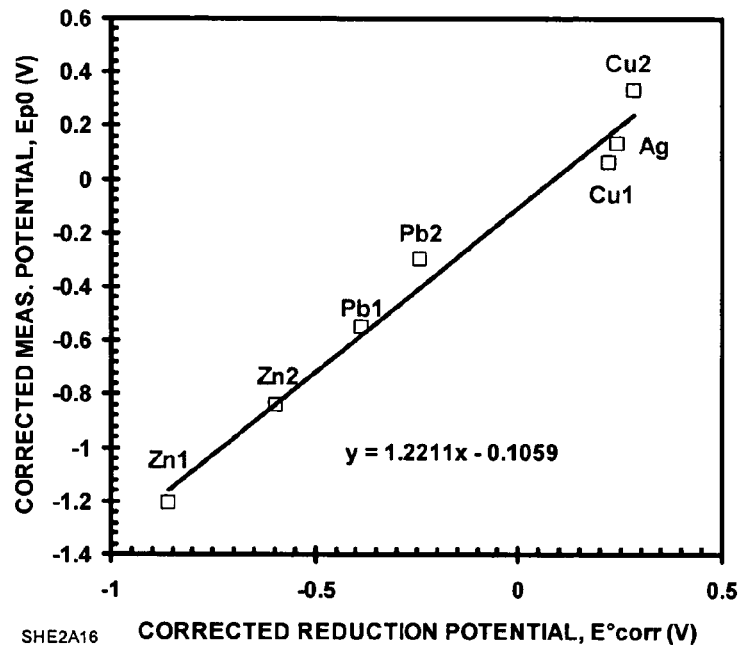
FIG. 20 is a table with ASV proposed reactions and potentials in volts.
FIG. 21 is a graph illustrating a linear relationship between measured and standard reduction potentials allowing tentative identification of the ionic species.

The possible reactions and their Reduction Potential, $E_o$ are listed in FIG. 20. The $E°$ values were corrected according to the ion concentration using the Nernst equation and are listed in the $E°_{corr}$ column. The $E_{\rho o}$ values determined from FIGS. 16 to 19 are listed in FIG. 20 along corrected $E_{\rho o}$ values using Eq. 10 and $\alpha = 0.5$.

The $E°_{corr}$ and $E_o$ values are plotted in FIG. 21 and show a remarkable linear relationship. As shown in the inset to this figure, the least squares fit to this data indicates a slope of 1.26 and intercept of −0.1 V. This curve when well established will serve as an aid in identifying ionic species.

B. First Sensor and Second Sensor Experimental Results

The following experiment describes results using ASV (Anodic Stripping Voltammetry) to achieve a detection limit, which in the case of Pb, is below one µM which is needed for water quality measurements. The richness of the detectable species is illustrated with Fe where seven species are identified using the Pourbiax diagram. The detection of multiple species is illustrated using Pb and Cu. The apparatus designed in accordance with the present invention, was used to detect the electroactivity of the metabolic-surrogate, PMS (Phenazine-methosulphate). Finally, four types of pH sensors were fabricated and characterized for linearity, sensitivity, and responsiveness.

(i) Introduction

Figure 22:
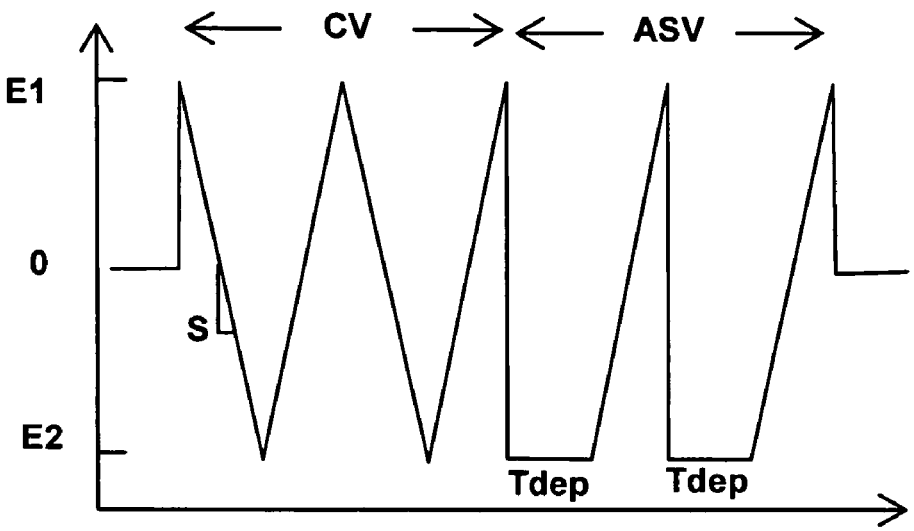
FIG. 22 is a plot of a waveform used to measure the redox sensors where S is the slope in mV/s and Tdep is deposition time in s.

The waveform applied to the redox cells is shown in FIG. 22. First CV (Cyclic Voltammetry) response is measured and then ASV (Anodic Stripping Voltammetry) response is measured after a deposition time, Tdep. Both CV and ASV responses are measured twice to validate the repeatability of the measurements. The magnitude of the waveform slope, S, is identical for both CV and ASV.

Typically E1=+1V and E2=−1V. These voltages are chosen to stay within the water electrolysis limits where oxygen is generated at the WE for positive potentials and hydrogen at negative potentials. The waveform is applied with Tdep values of 10, 20, 50, 100, 200, 500, and 100 s. For this Tdep sequence and S=20 mV/s, the measurement takes 132 minutes.

The experimental results are intended to illustrate both breadth of capability of this apparatus. First, the ASV response of $Fe(SO_4)_3$ illustrates how the many species of Fe can be identified using the Pourbiax diagram. Next, the requirements for low-level ion detection is described with $PbCl_2$ as an example. Next, the capability to detect multiple species is illustrated using $PbCl_2$ and $CuSO_4$. Then the detection of metabolic compound surrogate, PMS (phenazine-methosulphate) is described. Then, the fabrication of four types of PH sensors are described and characterized for linearity in their responses.

The ASV curves included in this application are recent results from the first sensor and the second sensor are shown for PMS.

(ii) ASV Iron Response

Figure 23:
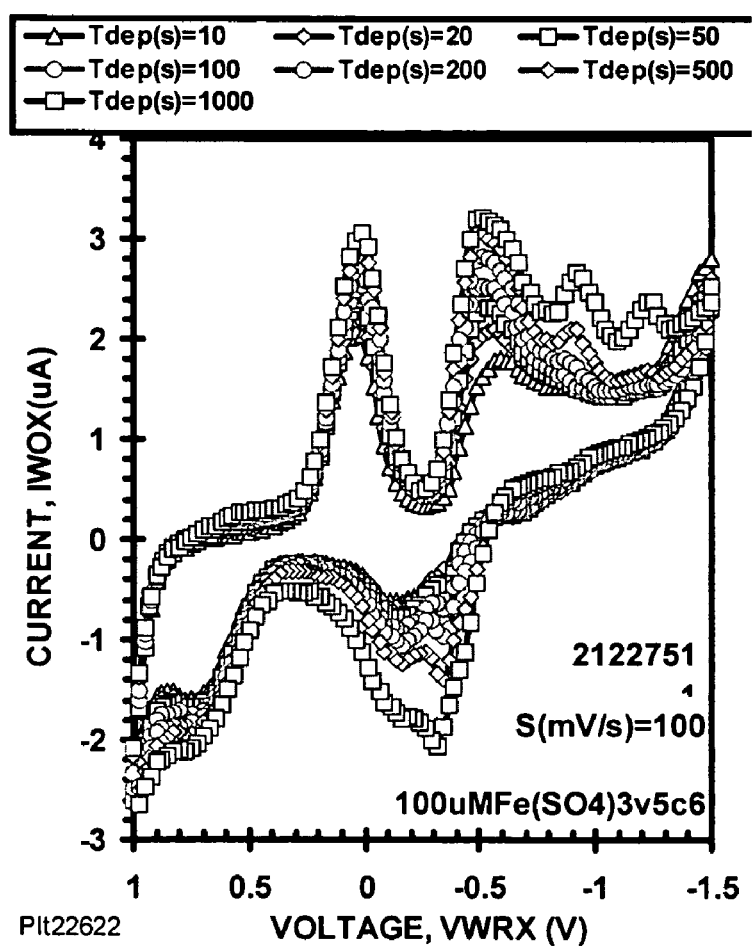
FIG. 23 is a graph illustrating a CV response of 100 $\mu M$ $Fe(SO_4)_3$, where Etg2: WE=Au, RE=Au, and AE=Au.

The CV response for 100 µM $Fe(SO_4)_3$ is shown in FIG. 23. It indicates that there are numerous electro-active species present. CV curves provide an overview of the species present in solution. In addition they display both reduction (positive to negative scan) and oxidation (negative to positive scan) reactions.

Figure 24:
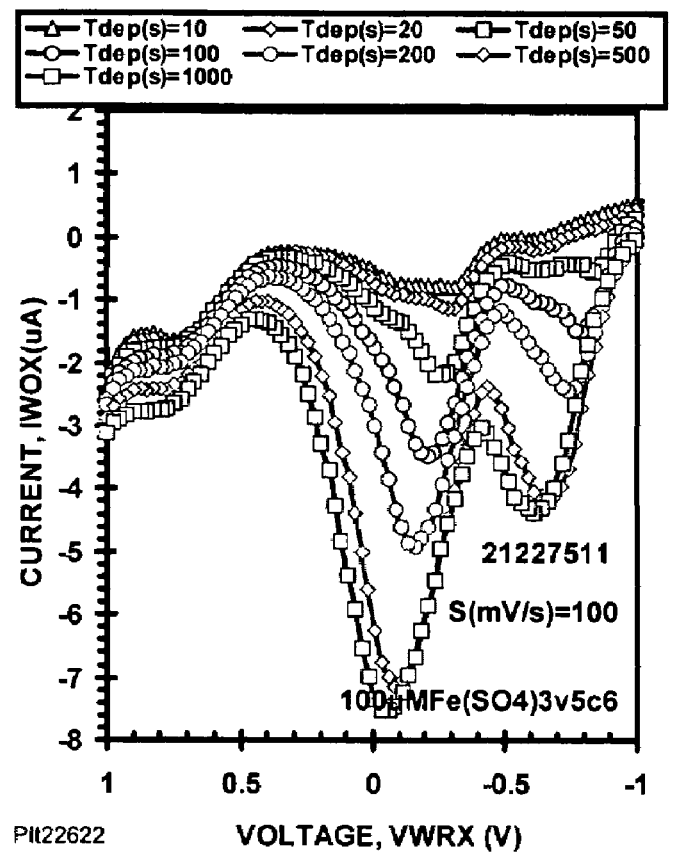
FIG. 24 is a graph illustrating ASV response of 100 $\mu M$ $Fe(SO_4)_3$, where Etg2: WE=Au, RE=Au, and AE=AU.

The ASV response, shown in FIG. 24, provides a look at reduction activity and is used to provide quantitative data regarding the species redox potential. In FIG. 24, the scan rate is S=100 mV/s and the Tdep follows a 1, 2, 5, sequence starting at 10 s and ending at 1000 s.

The identity of the ionic species is determined by matching the experimentally determined redox potentials at zero-peak current with known electrochemical potentials. The potential at zero-peak current is determined by extrapolating peak current-voltages to zero current. An Excel software routine, based on analyzing the second derivative of the ASV response, is used to find the peak current-voltages.

Figure 25:
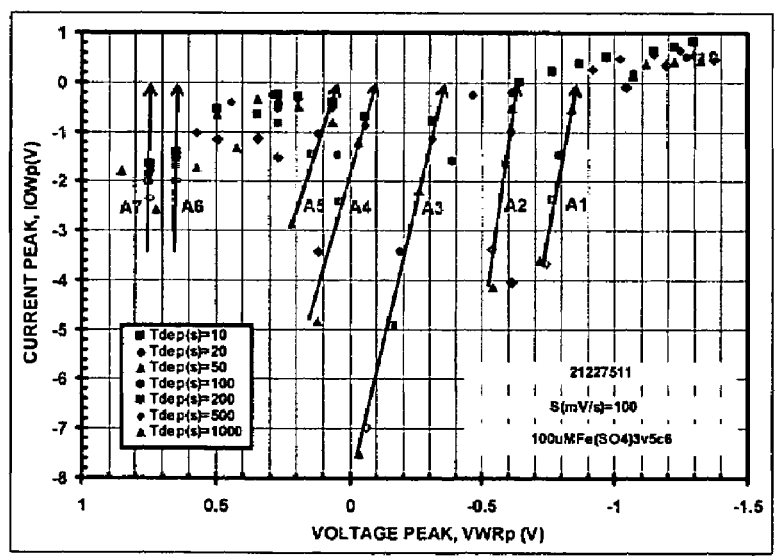
FIG. 25 is a graph illustrating peak response for 100 $\mu M$ $Fe(SO_4)_3$, where derived from FIG. 29.

The analysis of the ASV response for the peak current and voltages is shown in FIG. 25. It reveals that seven reactions are occurring at the WE. The identification of these reactions uses the Pourbaix diagram for iron shown in FIG. 25. During the ASV scan from −1 V to +1V the Pourbaix is traversed from A to B at pH=7. The oxidation reactions and their Nernst equations are listed in FIG. 26.

Figures 26, 27:
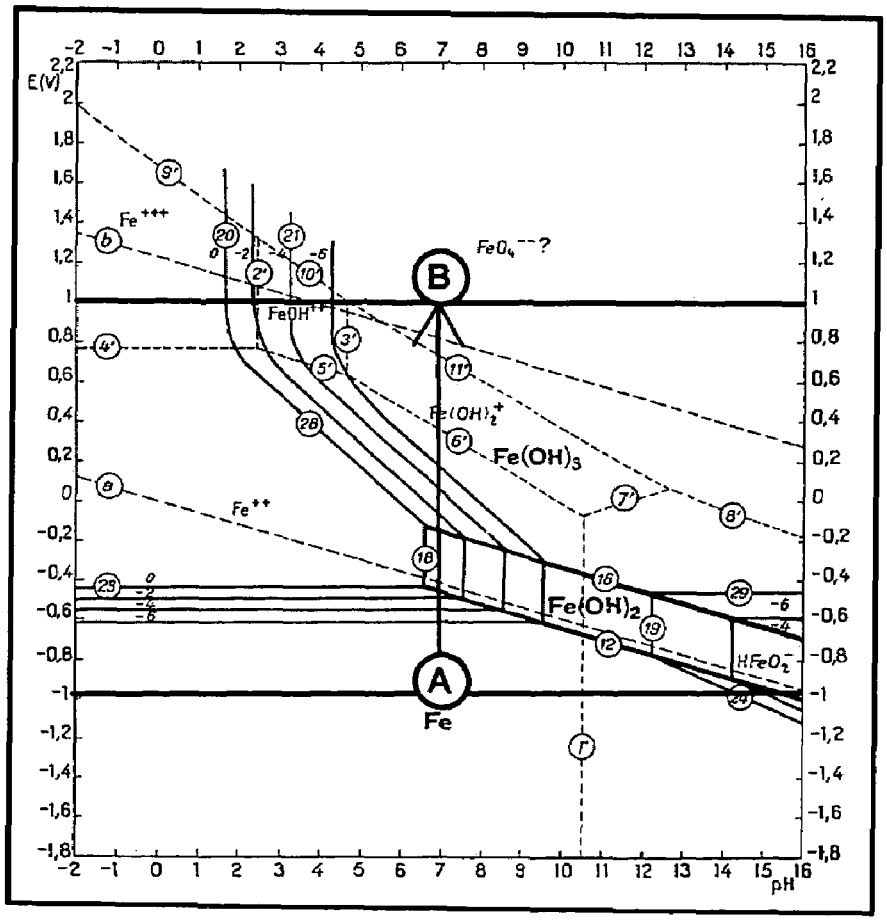
FIG. 26 is a table illustrating iron reactions for FIG. 25.
FIG. 27 is a graph illustrating a Pourbaix diagram for iron.

The reactions listed in FIG. 26 lead to the following sequence of reactions at the working electrode as the ASV potential is scanned from negative to positive potentials. The first reaction is iron entering solution as $Fe^{2+}$. Then iron combines with water to form the hydrate, $Fe(OH)_2$. This hydrate again combines with more water to form the hydrate $Fe(OH)_3$. Next iron is oxidized to $Fe^{3+}$. Finally $Fe^{2+}$ in solution near the WE forms $Fe^{3+}$.

Figure 28:
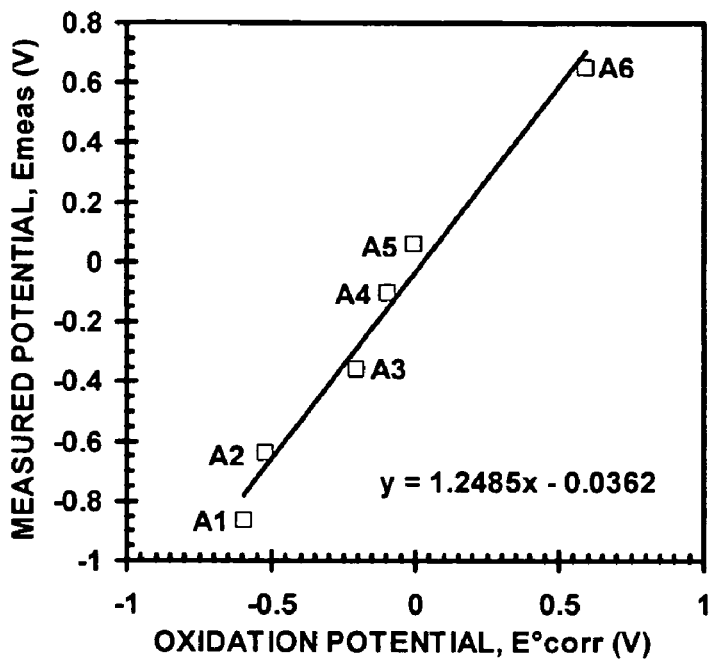
FIG. 28 is a graph illustrating a correlation between measured redox potentials derived from FIG. 26 and Pourbaix oxidation potentials derived from FIG. 27.

Peak voltages at zero current derived from FIG. 25 are combined with the potentials derived form the Pourbaix diagram for pH=7 and concentrations of 100 M. The result is shown in FIG. 28. The fitting equation is given in FIG. 28 and is y=1.2485x−0.0362. It indicates that the offset voltage is 36 mV and the slope is 1.24. This curve is used to relate the measured peak potentials at zero current to standard electrochemical potentials.

FIG. 28 is the correlation between measured redox potentials derived from FIG. 25 and Pourbaix oxidation potentials derived from FIG. 27.

(iii) Low-Level ASV Detection

Figure 29:
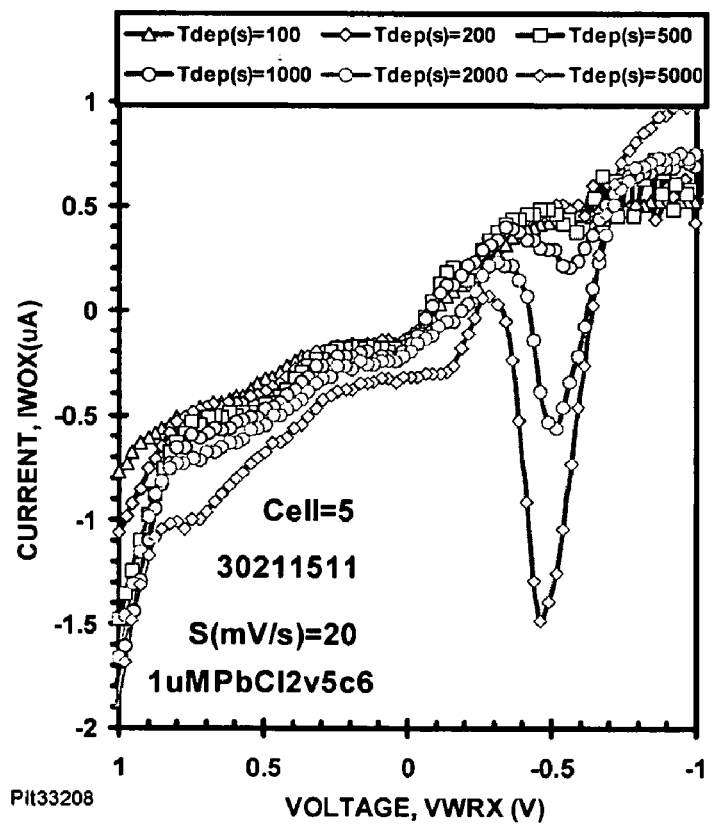
FIG. 29 is a graph illustrating ASV response of 1 $\mu M$ $PbCl_2$, where Etg2: WE=RE=AE=Au.

Low-level detection of ionic species is important when detecting residual ions in drinking water. The EPA allowable contamination limits for Pb is 0.2 µM. The ASV response of 1 µM of $PbCl_2$ is shown in FIG. 29. The peak response was achieved by increasing maximum Tdep from 1000 s to 5000 s. This means that low-level detection is possible but requires increased deposition times.

(iv) Lead/Copper ASV Response

In water quality measurements, the ability of ASV to measure multiple contaminates needs to be evaluated. An experiment was devised to determine the effectiveness of ASV to detect Pb and Cu. The oxidation of these cations is separated by about 0.5 V.

Figure 30:
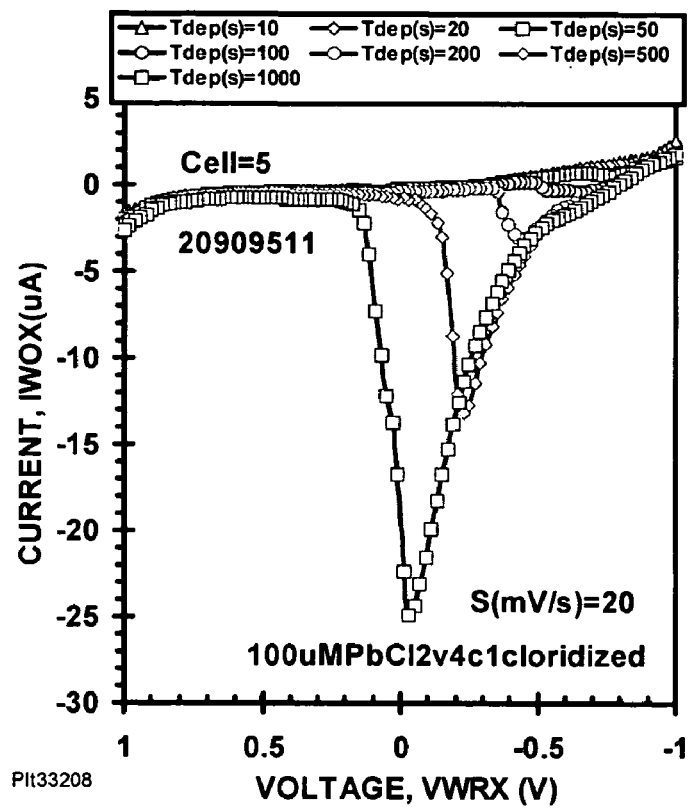
FIG. 30 is a graph illustrating ASV response of 100 $\mu M$ $PbCl_2$, where Etg2: WE=Au, RE=AgCl, AE=Au.
Figure 31:
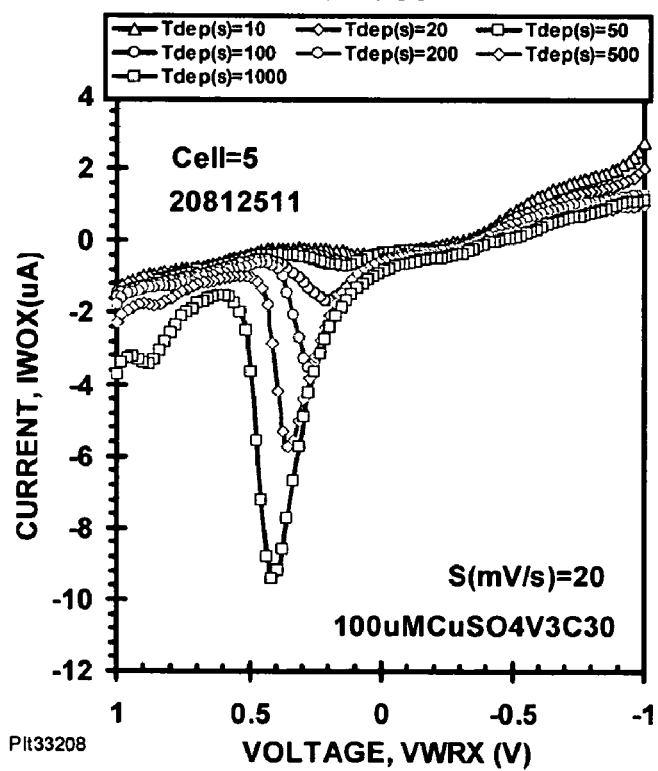
FIG. 31 is a graph illustrating ASV response of 100 $\mu M$ $CuSO_4$, where Etg2: WE=Au, RE=Au, AE=Au.
Figure 32:
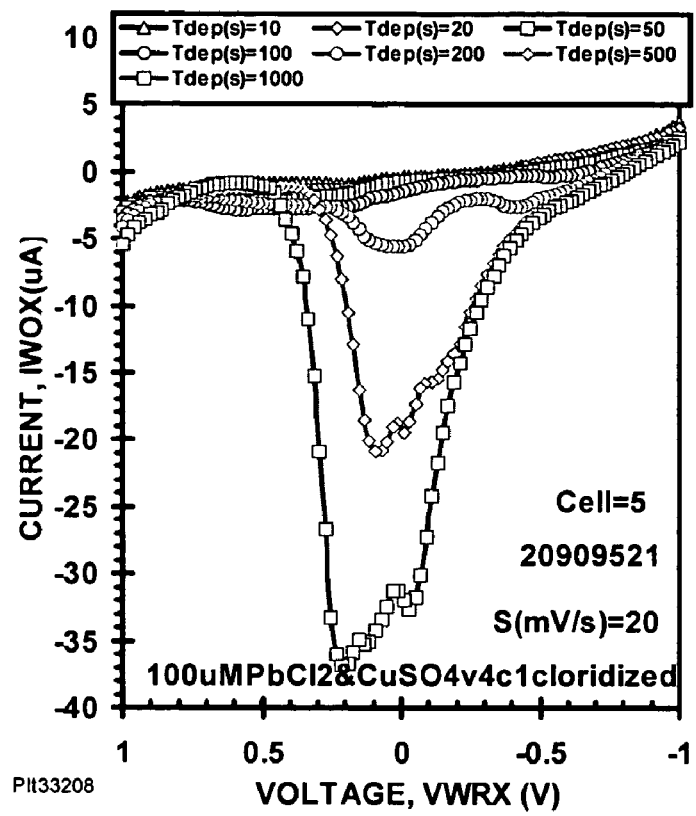
FIG. 32 is a graph illustrating ASV response of 100 $\mu M$ $PbCl_2$ and 100 $\mu M$ $CuSO_4$, where Etg2: WE=Au, RE=AgCl, AE=Au.
Figure 33:
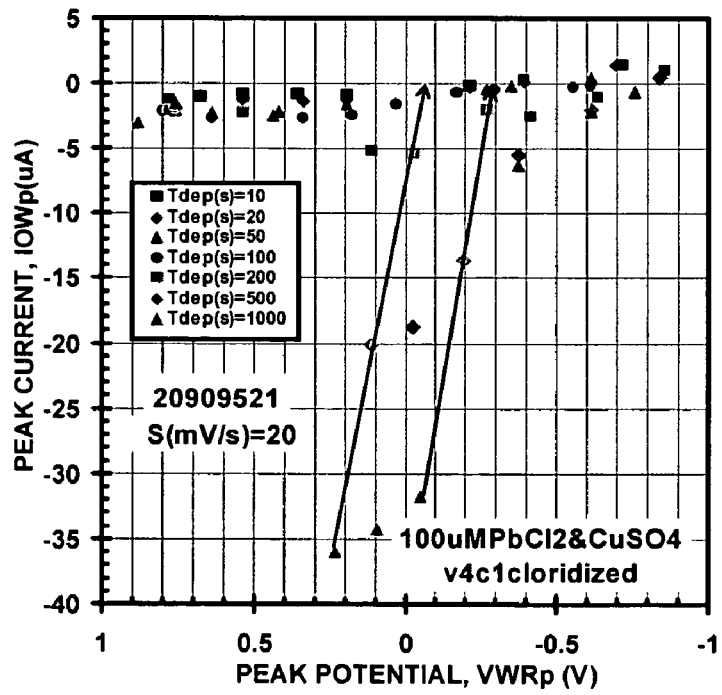
FIG. 33 is a graph illustrating peak current-voltage response of 100 $\mu M$ $PbCl_2$ and 100 $\mu M$ $CuSO_4$ derived from FIG. 32.

The individual ASV response of Pb and Cu are shown in FIGS. 30 and 31 respectively. The combined response is shown in FIG. 32. It is clear that Pb and Cu can be identified. Applying the second derivative analysis to this combined response leads to an identification of the peak potential at zero current as seen in FIG. 33.

(v) Microbial Electro-Active Species Response

Figure 34:
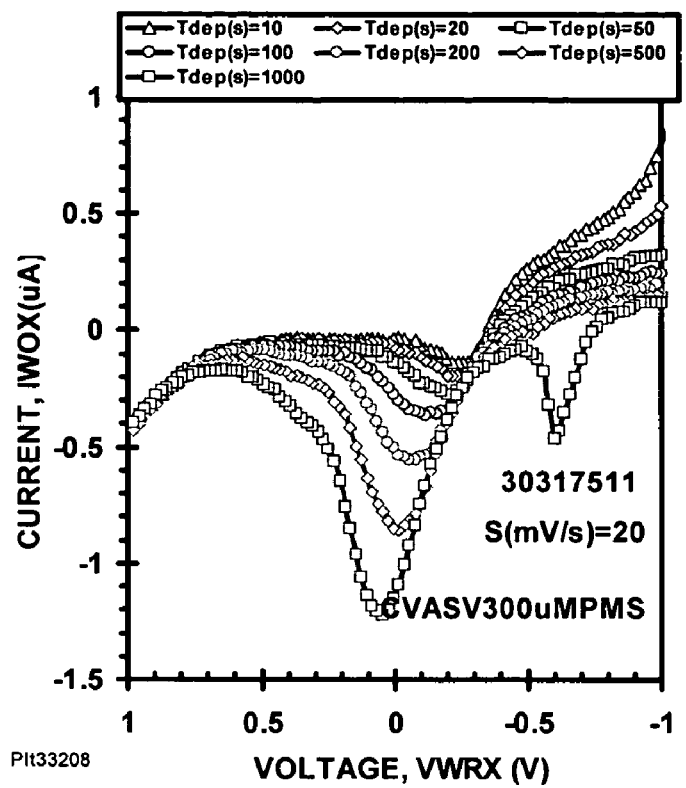
FIG. 34 is a graph illustrating ASV response of 300 $\mu M$ PMS, where Etg3, WE=Au, RE=Au, AE=Au.
Figure 35:
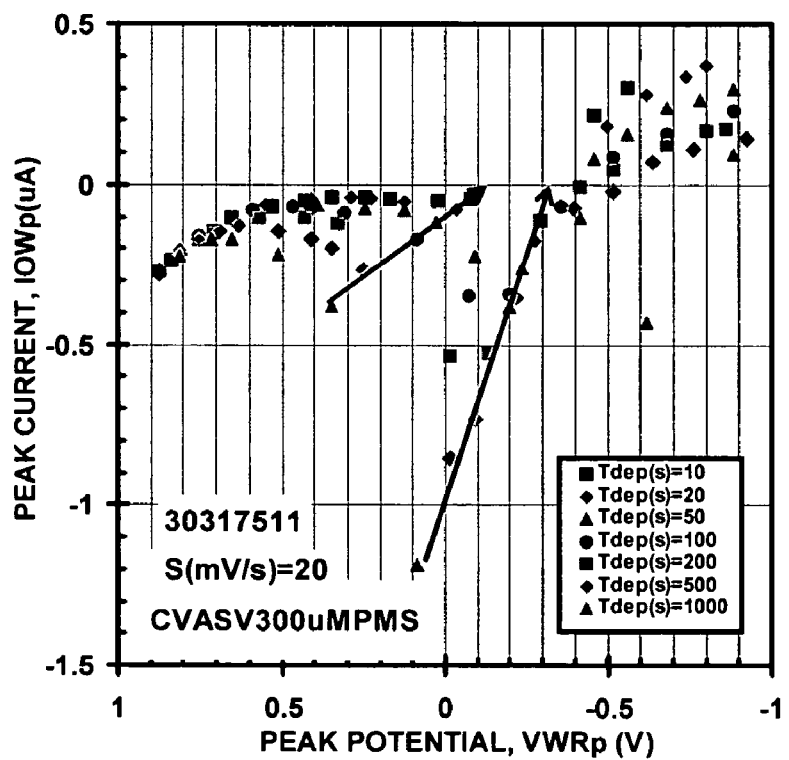
FIG. 35 is a graph illustrating peak current-voltage response of 300 $\mu M$ PMS derived from the ASV response in FIG. 34, where E1=-0.32V and E2=-0.12V.

E-Tongue 3 was designed to allow simultaneous observation of microbial growth and detection of their electro-active products. PMS (phenazine methosulfate) is a readily available compound that was used to simulate the ASV response of a microbial metabolic product. The response is shown in FIG. 34 and the peak current-voltage analysis is shown in FIG. 35. The analysis shows that two electro-active peaks are present. The peak that appears in the Tdep=1000 s curve in FIG. 34 has not been identified.

(vi) Response of pH Sensors

Knowledge of pH is critical in identifying electroactive species in solution. This need is supported by the dependence of the redox potentials on pH as seen in the Pourbaix diagram in FIG. 27. To fulfill this need, the four pH sensors listed in FIG. 37 were evaluated. They have fast response time, "drift-free" behavior, show good stability in aggressive environments and are compatible with planar geometries. The pH sensing materials were electrodeposited on gold substrates and integrated into E-Tongue 2.

Figures 38, 39:
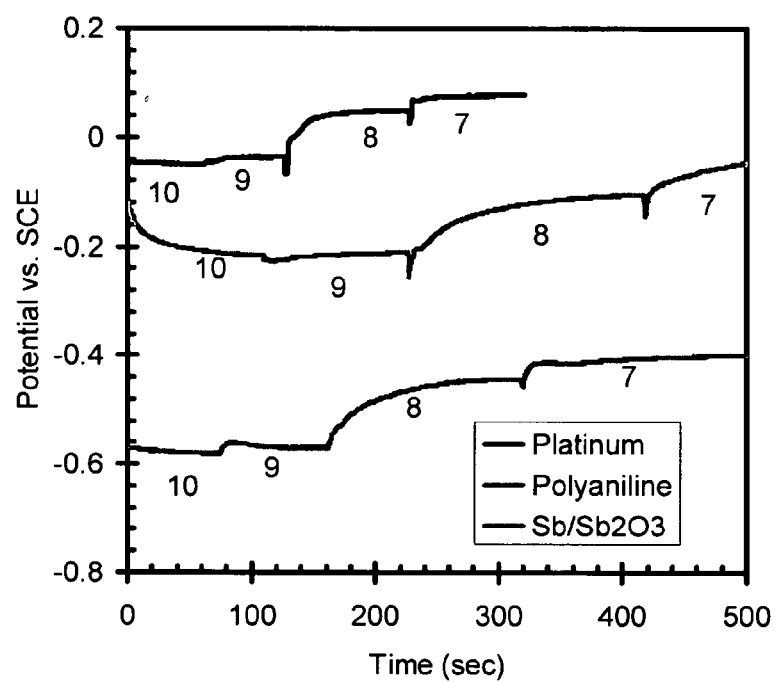
FIG. 38 is a table illustrating sensitivity of various pH sensing materials.
FIG. 39 is a graph illustrating dynamic pH response of Pt, Polyaniline, and $Sb/Sb_2O_3$ electrodes, where electrodeposited Ag/AgCl was used as reference electrodes.

FIG. 36 and FIG. 38 show the pH response of various electrodeposited sensing materials and their pH sensitivity. Polyaniline (i.e. conducting polymer) and iridium oxide (i.e. metal oxide) show high sensitivity of −85 mV/pH and −76 mV/pH, respectively, with linear response range from pH of 2 to 10. Antimony/antimony oxide electrode shows pH sensitivity of −55 mV/pH with greater detection range from pH of 0 to 12.

FIG. 39 shows the dynamic response of polyaniline, platinum, and antimony/antimony oxide electrodes with variation of pH from 10 to 7 using 1 v % $H_2SO_4$. Platinum and antimony/antimony oxide electrodes show fast response time (les than a few seconds) with good stability. In comparison to platinum and antimony/antimony oxide, the pH response time of polyaniline was slower. This might be due to thicker film thickness of polyaniline (approx. 10 micron) compared to platinum and antimony (<5 micron). In order to enhance the response time, the optimization of film thickness is in progress.

(8) Water Quality

The electro-active sensors may also be utilized to detect impurities in water. The next step in the development of water quality sensors is the development of repeatability and long-life sensors. The sensors may be used with any suitable water reclamation system, such as the one shown in FIG. 40. The system consists of gray water 4010 which enters the bioreactor 4004 where a number of impurities are converted by the microbes within the bioreactor.

Biological nitrification is a two-step process carried out by lithotrophic bacteria. Ammonia is oxidized to nitrite most commonly by bacteria of the genus Nitrosomonas by the following half reaction:

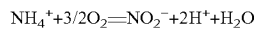

Nitrite is oxidized to nitrate by bacteria of the genus Nitrobacter by the half reaction:

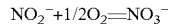

Figure 40:
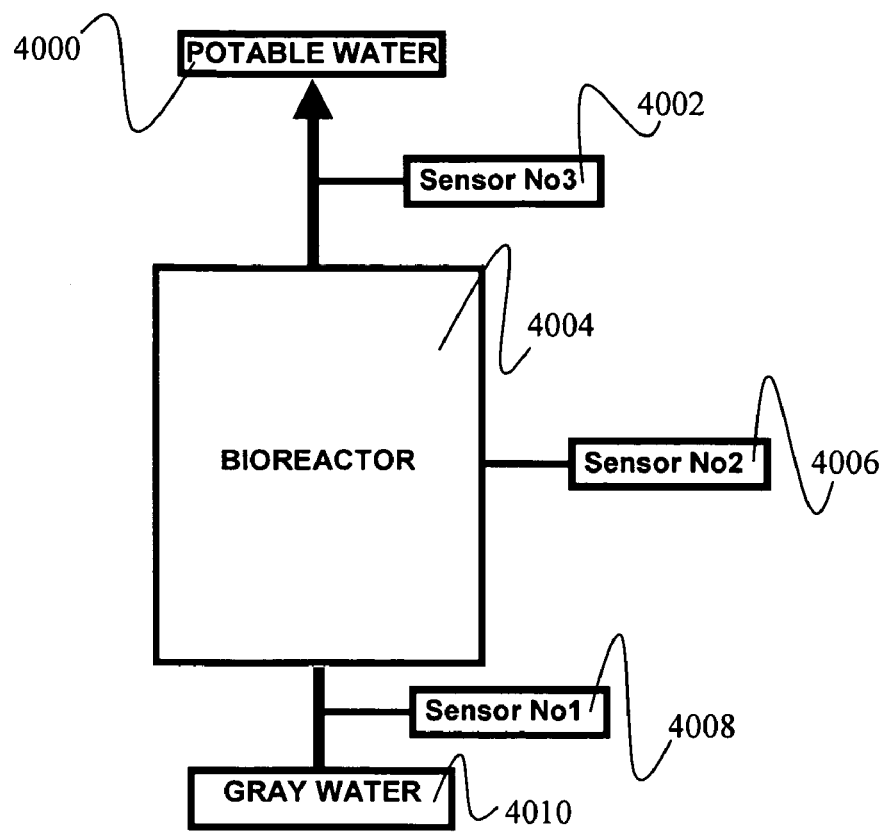
FIG. 40 is an illustration of a bioreactor system with sensors located to monitor a function of the bioreactor system.

The sensors location is indicated in FIG. 40. The sensors 4002, 4006, 4008 need to have adequate sensitivity and lifetime when exposed to various inorganics, organics, and biofilms. Sensors in the inlet line 4008 are exposed to gray water 4010, in the bioreactor the sensors 4006 are exposed directly to biofilms, and in the outlet line the sensors 4002 are exposed to clean water 4000. At the outlet, the sensors 4002 need to have high sensitivity in order to detect residual contaminants.

(9) Cleaning and Maintaining a Long-Life of the Electro-Active Sensors

Figure 41:
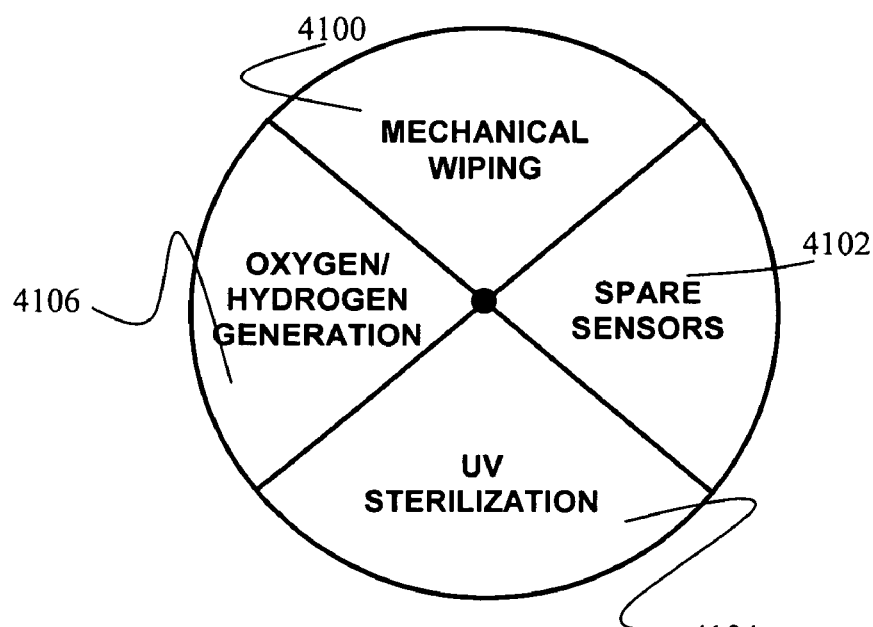
FIG. 41 is an illustration of cleaning and preservation methods for long-life bioreactor sensors.

An approach to long-life electro-active sensors uses the four cleaning and preservation methods depicted in FIG. 41 to maintain the surface of the electrochemical sensors in a state so that they provide data on the functioning of the bioreactor. Mechanical wiping 4100 is one approach but it is recognized that this approach could have limited applicability due to the build-up of biofilms on the wipers and scratching of sensitive films covering Ion Selective Electrodes.

An advantage of having multiple sensors in an array, such as is shown in FIG. 1, is sparing 4102. Through sparing 4102, individual sensors may be utilized, resulting in corrosion or an otherwise depletion of that individual sensors life usage. By using individual sensors in an array, as opposed to an entire array, the other sensors are spared. Through sparing 4102, unused sensors may be used later, thereby increasing a life-usage of the overall electro-active sensor.

(10) Conclusion

This application provides key insights into the fabrication and instrumentation of electro-active sensors. Use of the planar configuration opens up a number of application areas such as cleaning using wiping techniques and see-through chambers where the electrodes are fabricated opposite optically transparent windows. The ability to array the electrochemical cells with a common ground is critical in developing much larger sensor arrays. Understanding the conductivity sensor circuitry is critical in keeping it from interfering with the redox measurements. Finally, the analytical procedures developed on this effort are keys to identifying the nature of the electro-active species. The technique of extrapolating the peak current and voltage curve to zero current where $E_o$ is identified, is useful in determining possibilities for the nature of the electro-active species. This understanding provides the basis for the next phase of this effort in developing long life water quality sensors.

The electro-active sensors have the ability to detect a number of species in solution. In the case of Fe, six species were identified. In water quality measurements it is necessary to be able to identify more than one contaminant simultaneously. A mixture of $PbCl_2$ and $CuSO_4$ was characterized and the mixture response was significantly different from the individual responses. That is, the mixture showed double peaking; whereas, the individual responses did not. Low-level detection is also important for water quality. The detection limit for $PbCl_2$ was shown to be less than 1 μM requiring deposition times between 1000 and 5000 s. The apparatus was also used to detect organics, PMS. This compound is a metabolic product stimulant and its detection is important for both water quality and for future biofilm studies. Finally, four pH sensors were fabricated and characterized. They have good sensitivity and stability and will provide additional data needed to identify ionic species using Pourbaix diagrams.

What is claimed is:

1. An electro-active sensor for detecting electro-active species in solution, comprising:
   a nonconductive platform, the nonconductive platform having a first side and a second side;
   a first electrode set attached with the first side of the nonconductive platform, wherein the first electrode set further comprises:
   a first conductive via passing through the nonconductive platform from the first side to the second side;
   a first electrode attached with the first conductive via on the first side, where the first electrode serves as a first working electrode;
   a second conductive via passing through the nonconductive platform from the first side to the second side; a second electrode attached with the second conductive via on the first side, where the second electrode serves as a first reference electrode;
   a third conductive via passing through the nonconductive platform from the first side to the second side; and
   a third electrode attached with the third conductive via on the first side, where the third electrode serves as an first auxiliary electrode, whereby the working electrode, the reference electrode, and the auxiliary electrode serve as a electrochemical cell that may be utilized to detect the electro-active species in the solution;
   wherein the first auxiliary electrode from the first electrode set is connected with a second auxiliary electrode from a second electrode set; and
   wherein the first and second auxiliary electrodes are connected with a common ground.

2. An electro-active sensor as set forth in claim 1, wherein the electro-active sensor further comprises a plurality of electrode sets.

3. An electro-active sensor as set forth in claim 2, wherein the electro-active sensor further comprises electrical connectors connected with the vias on the second side of the nonconductive platform, whereby the electrical connectors may be connected with a monitoring apparatus, allowing for monitoring of the electro-active species in the solution.

4. An electro-active sensor as set forth in claim 3, wherein the nonconductive platform is constructed of a material selected from a group consisting of ceramic and glass.

5. An electro-active sensor as set forth in claim 4, wherein the electrodes are all formed in a substantially co-planar manner.

6. An electro-active sensor as set forth in claim 5, wherein the electrical connectors are substantially co-planar and a plane of the electrical connectors is parallel with respect to a plane of the nonconductive platform.

7. An electro-active sensor as set forth in claim 6, wherein at least a portion of each electrode in the electrode set is formed in a shape selected from a group consisting of a ring and a disk.

8. An electro-active sensor as set forth in claim 7, wherein each electrode set is formed such that the electrodes in the electrode set are concentric.

9. An electro-active sensor as set forth in claim 8, wherein the reference electrode surrounds the working electrode, and the auxiliary electrode surrounds the reference electrode.

10. An electro-active sensor as set forth in claim 9, wherein the electro-active sensor further comprises a biofilm attached with the first side of the nonconductive platform.

11. An electro-active sensor as set forth in claim 10, wherein the electro-active sensor further comprises an Ion Selective Sensor attached with the first side of the nonconductive platform.

12. An electro-active sensor as set forth in claim 11, wherein the Ion Selective Sensor is a pH sensor.

13. An electro-active sensor as set forth in claim 12, wherein the electro-active sensor further comprises a four-terminal conductivity sensor attached with the first side of the nonconductive platform, thereby allowing for a measurement of a conductivity of the solution.

14. An electro-active sensor as set forth in claim 13, wherein the electro-active sensor further comprises a two-terminal heater attached with the nonconductive platform, thereby allowing the electro-active sensor to be heated to varying temperatures.

15. An electro-active sensor as set forth in claim 14, wherein the electro-active sensor further comprises a two-terminal temperature sensor attached with the nonconductive platform, thereby allowing for monitoring of a temperature of the electro-active sensor.

16. An electro-active sensor as set forth in claim 15, wherein the electro-active sensor further comprises circuitry attached with the electrical connectors, the circuitry further comprising: a potentiostat circuit portion attached with an electrochemical cell, the electrochemical cell comprising a grounded auxiliary electrode, a reference electrode, and a working electrode, whereby when activated, the potentiostat circuit portion forces a voltage between the working electrode and the reference electrode; a feedback circuit connected with the potentiostat circuit portion, whereby when the potentiostat circuit portion is activated, the feedback circuit adjusts a current though the electrochemical cell accordingly; a galvanostat circuit portion attached with the electrochemical cell, whereby the galvanostat circuit portion forces a current through the electrochemical cell and when the galvanostat circuit portion is activated the feedback circuit adjusts a voltage between the working electrode and the reference electrode; and a switch circuit connected with the potentiostat circuit portion and galvanostat circuit portion, allowing for the activation of the potentiostat or galvanostat circuit portion.

17. An electro-active sensor as set forth in claim 1, wherein the electro-active sensor further comprises electrical connectors connected with the vias on the second side of the nonconductive platform, whereby the electrical connectors may be connected with a monitoring apparatus, allowing for monitoring of the electro-active species in the solution.

18. An electro-active sensor as set forth in claim 17, wherein the electrical connectors are substantially co-planar and a plane of the electrical connectors is parallel with respect to a plane of the nonconductive platform.

19. An electro-active sensor as set forth in claim 1, wherein the nonconductive platform is constructed of a material selected from a group consisting of ceramic and glass.

20. An electro-active sensor as set forth in claim 1, wherein the electrodes are all formed in a substantially co-planar manner.

21. An electro-active sensor as set forth in claim 1, wherein at least a portion of each electrode in the electrode set is formed in a shape selected from a group consisting of a ring and a disk.

22. An electro-active sensor as set forth in claim 1, wherein each electrode set is formed such that the electrodes in the electrode set are concentric.

23. An electro-active sensor as set forth in claim 1, wherein the reference electrode surrounds the working electrode, and the auxiliary electrode surrounds the reference electrode.

24. An electro-active sensor as set forth in claim 1, wherein the electro-active sensor further comprises a biofilm attached with the first side of the nonconductive platform.

25. An electro-active sensor as set forth in claim 1, wherein the electro-active sensor further comprises an Ion Selective Sensor attached with the first side of the nonconductive platform.

26. An electro-active sensor as set forth in claim 25, wherein the Ion Selective Sensor is a pH sensor.

27. An electro-active sensor as set forth in claim 1, wherein the electro-active sensor further comprises a four-terminal conductivity sensor attached with the first side of the nonconductive platform, thereby allowing for a measurement of a conductivity of the solution.

28. An electro-active sensor as set forth in claim 1, wherein the electro-active sensor further comprises a two-terminal heater attached with the nonconductive platform, thereby allowing the electro-active sensor to be heated to varying temperatures.

29. An electro-active sensor as set forth in claim 1, wherein the electro-active Sensor further comprises a two-terminal temperature sensor attached with the nonconductive platform, thereby allowing for monitoring of a temperature of the electro-active sensor.

30. An electro-active sensor as set forth in claim 1, wherein the electro-active sensor further comprises circuitry attached with the electrical connectors, the circuitry further comprising: a potentiostat circuit portion attached with an electrochemical cell, the electrochemical cell comprising a grounded auxiliary electrode, a reference electrode, and a working electrode, whereby when activated, the potentiostat circuit portion forces a voltage between the working electrode and the reference electrode; a feedback circuit connected with the potentiostat circuit portion, whereby when the potentiostat circuit portion is activated, the feedback circuit adjusts a current though the electrochemical cell accordingly; a galvanostat circuit portion attached with the electrochemical cell, whereby the galvanostat circuit portion forces a current through the electrochemical cell and when the galvanostat circuit portion is activated the feedback circuit adjusts a voltage between the working electrode and the reference electrode; and a switch circuit connected with the potentiostat circuit portion and galvanostat circuit portion, allowing for the activation of the potentiostat or galvanostat circuit portion.

\* \* \* \* \*

UNITED STATES PATENT AND TRADEMARK OFFICE
CERTIFICATE OF CORRECTION

PATENT NO. : 7,578,912 B2  Page 1 of 1
APPLICATION NO. : 10/750162
DATED : August 25, 2009
INVENTOR(S) : Martin Buehler It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1591 days.

Signed and Sealed this

Fourteenth Day of September, 2010

David J. Kappos
*Director of the United States Patent and Trademark Office*